(12) United States Patent
Medeiros et al.

(10) Patent No.: US 12,349,945 B2
(45) Date of Patent: *Jul. 8, 2025

(54) PATIENT-MOUNTED SURGICAL SUPPORT

(71) Applicant: Medos International Sarl, Le Locle (CH)

(72) Inventors: Andrew Medeiros, Fall River, MA (US); Zoher Bootwala, Foxboro, MA (US); Nicholas Miller, Raynham, MA (US); Roman Lomeli, Plymouth, MA (US)

(73) Assignee: Medos International Sàrl, Le Locle (CH)

( * ) Notice: Subject to any disclaimer, the term of this patent is extended or adjusted under 35 U.S.C. 154(b) by 7 days.

This patent is subject to a terminal disclaimer.

(21) Appl. No.: 18/344,490

(22) Filed: Jun. 29, 2023

(65) Prior Publication Data
US 2023/0414259 A1 Dec. 28, 2023

Related U.S. Application Data

(63) Continuation of application No. 17/168,004, filed on Feb. 4, 2021, now Pat. No. 11,723,697, which is a
(Continued)

(51) Int. Cl.
*A61B 17/70* (2006.01)
*A61B 17/02* (2006.01)
(Continued)

(52) U.S. Cl.
CPC ...... *A61B 17/7077* (2013.01); *A61B 17/0206* (2013.01); *A61B 17/025* (2013.01);
(Continued)

(58) Field of Classification Search
CPC ............ A61B 17/7083; A61B 17/7086; A61B 17/708; A61B 17/7077; A61B 17/7076
See application file for complete search history.

(56) References Cited

U.S. PATENT DOCUMENTS

| 4,874,375 A | 10/1989 | Ellison |
| 5,728,046 A | 3/1998 | Mayer et al. |

(Continued)

FOREIGN PATENT DOCUMENTS

| CN | 101489497 8 | 1/2011 |
| CN | 103442656 B | 4/2016 |

(Continued)

OTHER PUBLICATIONS

[No Author Listed] MIT Lateral Platform, "Surgical Technique Guide," DePuy Spine Inc., 2012.
(Continued)

*Primary Examiner* — Julianna N Harvey
(74) *Attorney, Agent, or Firm* — Barnes & Thornburg LLP

(57) ABSTRACT

Surgical support instruments are described herein that can couple to, e.g., an implanted anchor and provide a platform for coupling other surgical implements thereto. In one embodiment, an instrument can include an elongate body having opposed projections extending laterally from a distal portion thereof that can at least partially surround a shank of an implantable anchor such that a longitudinal axis of the elongate body is laterally offset from a longitudinal axis of the anchor. The instrument can further include a lock configured to exert a drag force on a head of the anchor to control polyaxial movement of the instrument relative to the anchor. Further, a proximal portion of the elongate body can be configured to receive a retractor assembly including a plurality of tissue manipulating implements and selectively lock the retractor assembly at any of a plurality of positions along a length of the elongate body.

20 Claims, 34 Drawing Sheets

Related U.S. Application Data continuation of application No. 16/139,409, filed on Sep. 24, 2018, now Pat. No. 10,945,773.

(60) Provisional application No. 62/562,055, filed on Sep. 22, 2017, provisional application No. 62/562,046, filed on Sep. 22, 2017.

(51) Int. Cl.
| | | |
|---|---|---|
| *A61B 17/29* | (2006.01) | |
| *A61B 90/50* | (2016.01) | |
| *A61B 90/57* | (2016.01) | |
| *A61B 90/60* | (2016.01) | |
| *A61F 2/30* | (2006.01) | |
| *A61B 17/00* | (2006.01) | |
| *A61B 17/86* | (2006.01) | |
| *A61B 90/00* | (2016.01) | |

(52) U.S. Cl.
CPC .......... *A61B 17/29* (2013.01); *A61B 17/7032* (2013.01); *A61B 17/7076* (2013.01); *A61B 17/708* (2013.01); *A61B 90/50* (2016.02); *A61B 90/57* (2016.02); *A61B 90/60* (2016.02); *A61F 2/30* (2013.01); *A61B 2017/003* (2013.01); *A61B 2017/00398* (2013.01); *A61B 2017/0256* (2013.01); *A61B 17/8625* (2013.01); *A61B 17/863* (2013.01); *A61B 2090/062* (2016.02); *A61B 2090/571* (2016.02)

(56) References Cited

U.S. PATENT DOCUMENTS

| | | |
|---|---|---|
| 5,902,233 A | 5/1999 | Farley et al. |
| 5,931,777 A | 8/1999 | Sava |
| 5,944,658 A | 8/1999 | Koros et al. |
| 6,083,154 A | 7/2000 | Liu et al. |
| 6,869,398 B2 | 3/2005 | Obenchain et al. |
| 6,951,538 B2 | 10/2005 | Ritland |
| 7,014,608 B2 | 3/2006 | Larson et al. |
| 7,179,261 B2 | 2/2007 | Sicvol et al. |
| 7,491,168 B2 | 2/2009 | Raymond et al. |
| 7,918,792 B2 | 4/2011 | Drzyzga et al. |
| 7,959,564 B2 | 6/2011 | Ritland |
| 8,182,519 B2 | 5/2012 | Loftus et al. |
| 8,202,216 B2 | 6/2012 | Melkent et al. |
| 8,357,184 B2 | 1/2013 | Woolley et al. |
| 8,394,109 B2 | 3/2013 | Hutton et al. |
| 8,409,087 B2 | 4/2013 | Amnes et al. |
| 8,435,269 B2 | 5/2013 | Woolley et al. |
| 8,469,960 B2 | 6/2013 | Hutton et al. |
| 8,535,320 B2 | 9/2013 | Woolley et al. |
| 8,636,655 B1 | 1/2014 | Childs |
| 8,668,715 B2 | 3/2014 | Sandhu |
| 8,882,661 B2 | 11/2014 | Hutton et al. |
| 8,894,573 B2 | 11/2014 | Loftus et al. |
| 8,900,137 B1 | 12/2014 | Lovell et al. |
| 8,911,442 B2 | 12/2014 | Wing et al. |
| 8,974,381 B1 | 3/2015 | Lovell et al. |
| 9,050,146 B2 | 6/2015 | Woolley et al. |
| 9,216,016 B2 | 12/2015 | Flechter et al. |
| 9,307,972 B2 | 4/2016 | Lovell et al. |
| 9,386,971 B1 | 7/2016 | Casey et al. |
| 9,414,828 B2 | 8/2016 | Abidin et al. |
| 9,572,560 B2 | 2/2017 | Mast et al. |
| 9,615,818 B2 | 4/2017 | Baudouin et al. |
| 9,649,099 B1 | 5/2017 | Casey et al. |
| 9,693,762 B2 | 7/2017 | Reimels |
| 9,700,293 B2 | 7/2017 | Cryder et al. |
| 9,801,667 B2 | 10/2017 | Hawkes et al. |
| 9,844,400 B2 | 12/2017 | Stevenson et al. |
| 9,907,583 B2 | 3/2018 | Hayes |
| 10,463,402 B2 | 11/2019 | Biester et al. |
| 10,792,168 B2 | 10/2020 | Malcolmson et al. |
| 10,945,773 B2 | 3/2021 | Medeiros et al. |
| 11,559,372 B2 | 1/2023 | Medeiros et al. |
| 11,723,697 B2 * | 8/2023 | Medeiros ............... A61B 17/29 600/235 |
| 2004/0230191 A1 | 11/2004 | Frey et al. |
| 2005/0131408 A1 | 6/2005 | Sicvol et al. |
| 2005/0131422 A1 | 6/2005 | Anderson et al. |
| 2005/0228400 A1 | 10/2005 | Chao et al. |
| 2005/0245929 A1 | 11/2005 | Winslow et al. |
| 2006/0052671 A1 | 3/2006 | McCarthy |
| 2007/0093823 A1 | 4/2007 | Booth et al. |
| 2007/0191955 A1 | 8/2007 | Zucherman et al. |
| 2007/0213715 A1 | 9/2007 | Bridwell et al. |
| 2007/0270869 A1 | 11/2007 | Young et al. |
| 2008/0021285 A1 | 1/2008 | Drzyzga et al. |
| 2008/0140120 A1 | 6/2008 | Hestad et al. |
| 2008/0262318 A1 | 10/2008 | Gorek et al. |
| 2009/0036746 A1 | 2/2009 | Blackwell et al. |
| 2009/0093684 A1 | 4/2009 | Schorer |
| 2009/0149885 A1 | 6/2009 | Durward et al. |
| 2009/0187080 A1 | 7/2009 | Seex |
| 2009/0203969 A1 | 8/2009 | Cohen et al. |
| 2010/0317928 A1 | 12/2010 | Subramaniam |
| 2011/0004248 A1 | 1/2011 | Abdou |
| 2011/0034779 A1 | 2/2011 | Louftus et al. |
| 2011/0130793 A1 | 6/2011 | Woolley et al. |
| 2011/0137345 A1 | 6/2011 | Stoll et al. |
| 2011/0196426 A1 | 8/2011 | Peukert et al. |
| 2012/0089150 A1 | 4/2012 | Smith |
| 2012/0232350 A1 | 9/2012 | Seex |
| 2013/0310942 A1 | 11/2013 | Abdou |
| 2013/0345755 A1 | 12/2013 | Prajapati et al. |
| 2014/0074166 A1 | 3/2014 | Scarrow et al. |
| 2014/0194697 A1 | 7/2014 | Seex |
| 2014/0277163 A1 | 9/2014 | Kretzer et al. |
| 2014/0296917 A1 | 10/2014 | Donner et al. |
| 2015/0148853 A1 | 5/2015 | Hawkes et al. |
| 2015/0313585 A1 | 11/2015 | Abidin et al. |
| 2016/0015433 A1 | 1/2016 | Jackson |
| 2016/0030029 A1 | 2/2016 | Mahoney et al. |
| 2016/0074029 A1 * | 3/2016 | O'Connell ............ A61B 17/02 600/215 |
| 2016/0106408 A1 | 4/2016 | Ponmudi et al. |
| 2016/0296220 A1 | 10/2016 | Mast et al. |
| 2016/0354073 A1 | 12/2016 | Nel et al. |
| 2017/0035406 A1 | 2/2017 | Abidin et al. |
| 2017/0105770 A1 | 4/2017 | Woolley et al. |
| 2017/0135735 A1 | 5/2017 | Hawkes et al. |
| 2017/0265850 A1 | 9/2017 | Cryder et al. |
| 2018/0014858 A1 | 1/2018 | Biester et al. |
| 2019/0090864 A1 | 3/2019 | Medeiros et al. |
| 2019/0090979 A1 | 3/2019 | Medeiros et al. |
| 2021/0196326 A1 | 7/2021 | Medeiros et al. |
| 2023/0136167 A1 | 5/2023 | Medeiros et al. |

FOREIGN PATENT DOCUMENTS

| | | |
|---|---|---|
| CN | 105611883 A | 5/2016 |
| CN | 102821673 B | 6/2016 |
| CN | 106793940 B | 2/2019 |
| JP | 2009528134 A | 8/2009 |
| JP | 2017528197 A | 9/2017 |
| WO | 2010121291 A1 | 10/2010 |
| WO | 2016131077 A1 | 8/2016 |

OTHER PUBLICATIONS

[No Author Listed] [No Date Given] "NuVasive MAS TLIF Surgical Technique," (25 pages).

[No Author Listed] "NuVasive MAS TLIF 2 Surgical Technique," NuVasive Inc., 2016 (48 pages).

[No Author Listed] Pipeline Access System and CONCORDE, "Surgical Technique—Guide and Protect Catalogue," DePuy Spine Inc., 2011.

[No Author Listed] "Click'X System Surgical Technique Guide," DePuy Spine Inc., 2015 (52 pages).

[No Author Listed] "Point to Point Minimally Invasive Retractor System Technique Guide," Synthes Spine, 2006 (24 pages).

(56) References Cited

OTHER PUBLICATIONS

Chinese Office Action for Application No. 201880075167.0, issued Jul. 14, 2022 (88041-341080) (17 pages).
Chinese Office Action for Application No. 201880075167.0, issued Nov. 24, 2021 (18 pages).
Partial European Search Report for European Application No. 18857923.9, issued Sep. 24, 2021 (14 pages).
Extended European Search Report for European Application No. 18857923.9, issued Feb. 24, 2022 (19 pages).
Extended European Search Report for European Application No. 18858218.3, issued Jun. 2, 2021 (9 pages).
International Preliminary Report on Patentability for Application No. PCT/US2018/044631, mailed Dec. 12, 2018 (10 pages).
International Search Report and Written Opinion for Application No. PCT/US2018/044631, mailed Dec. 12, 2018 (15 pages).
International Search Report and Written Opinion for Application No. PCT/IB18/57366, dated Jan. 18, 2019 (8 pages).
International Search Report and Written Opinion for Application No. PCT/IB18/57367, mailed Jan. 29, 2019, (10 pages).
Japanese Office Action for Application No. 2020-516705, issued Jun. 28, 2022 (10 pages).
Japanese Office Action for Application No. 2020-516582, issued Jun. 21, 2022 (10 pages).
Chinese Office Action for Application No. 201880075114.9, issued Aug. 31, 2023 (18 pages).

\* cited by examiner

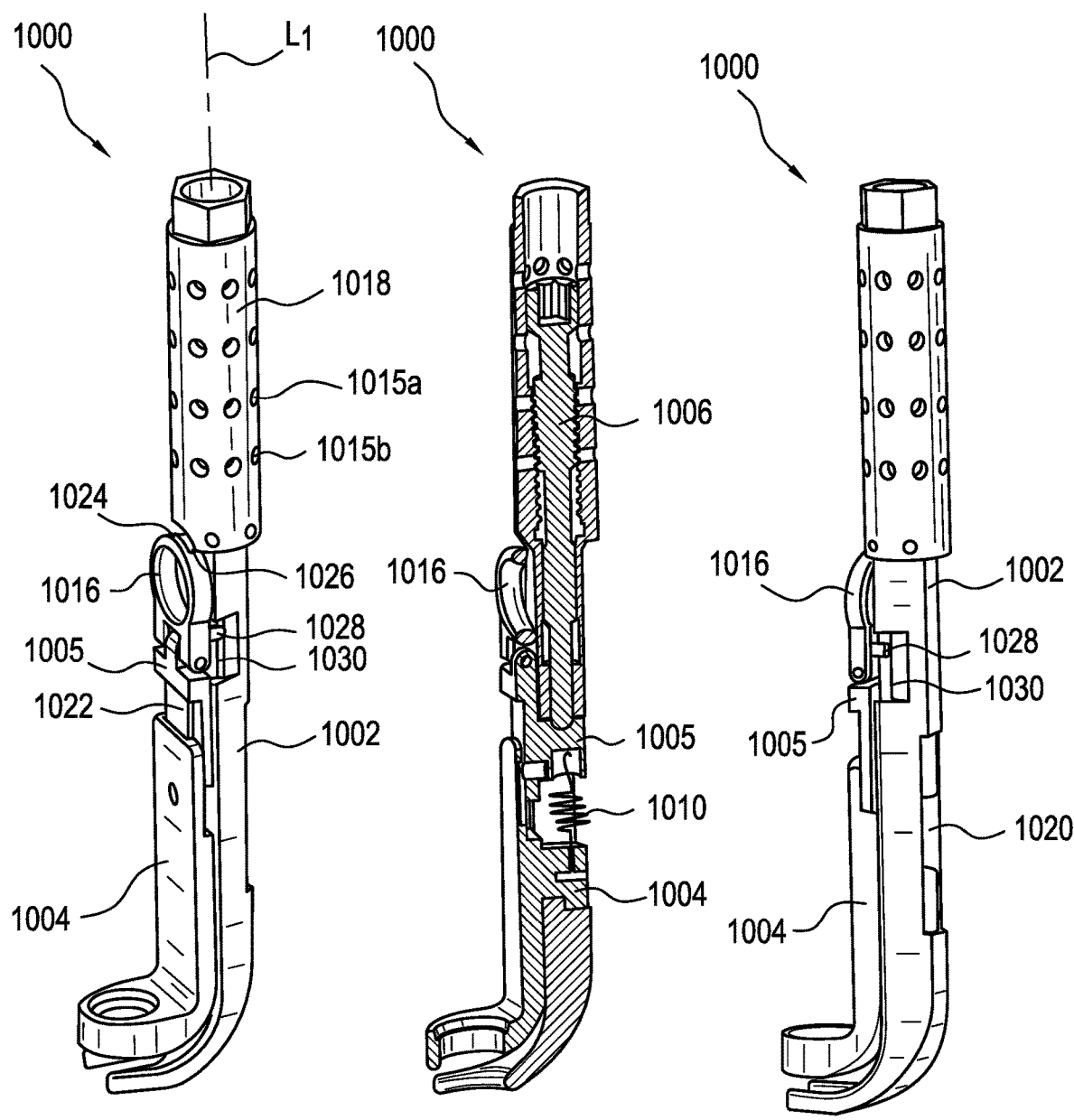

FIG. 21
FIG. 22
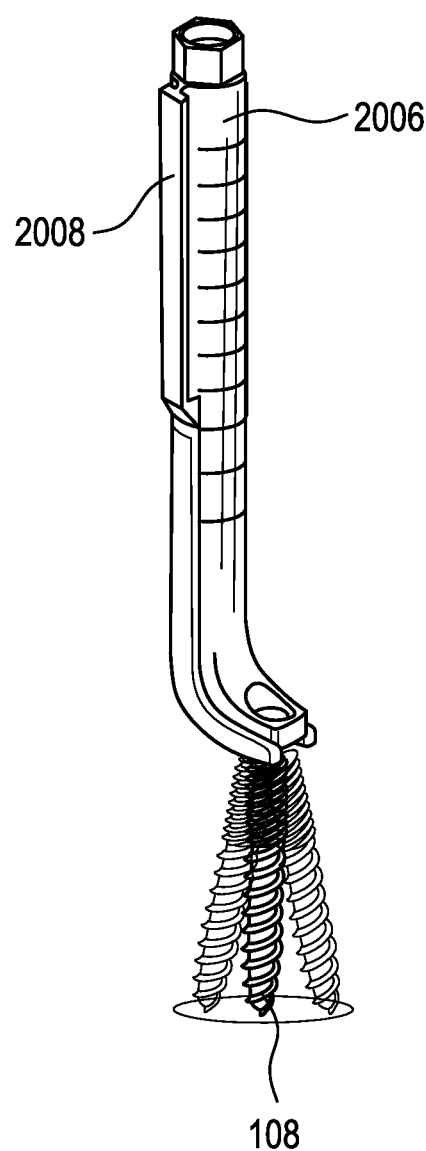
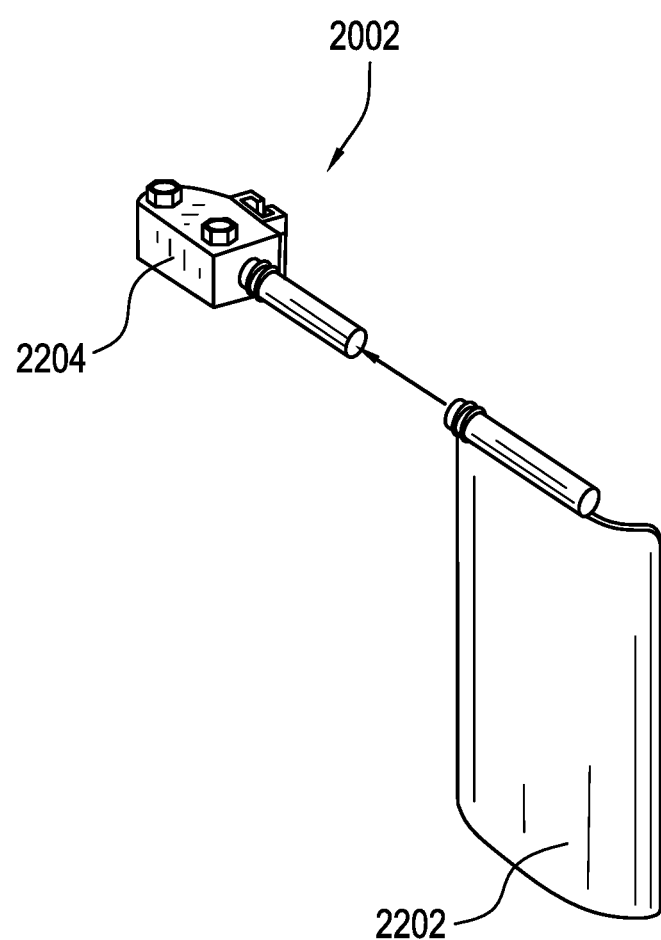

FIG. 36A
FIG. 36C
FIG. 36B
FIG. 36D
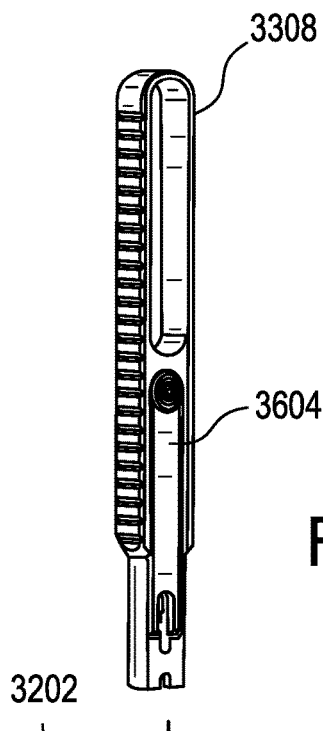
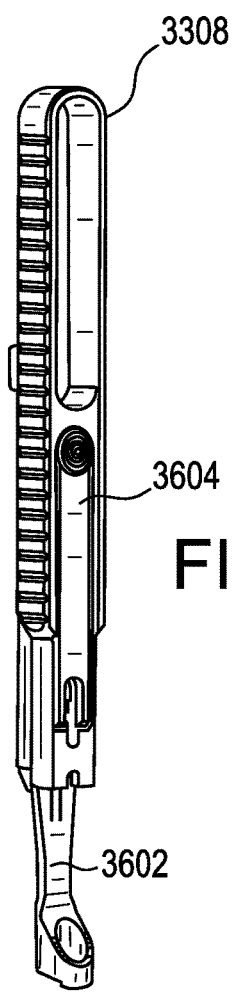
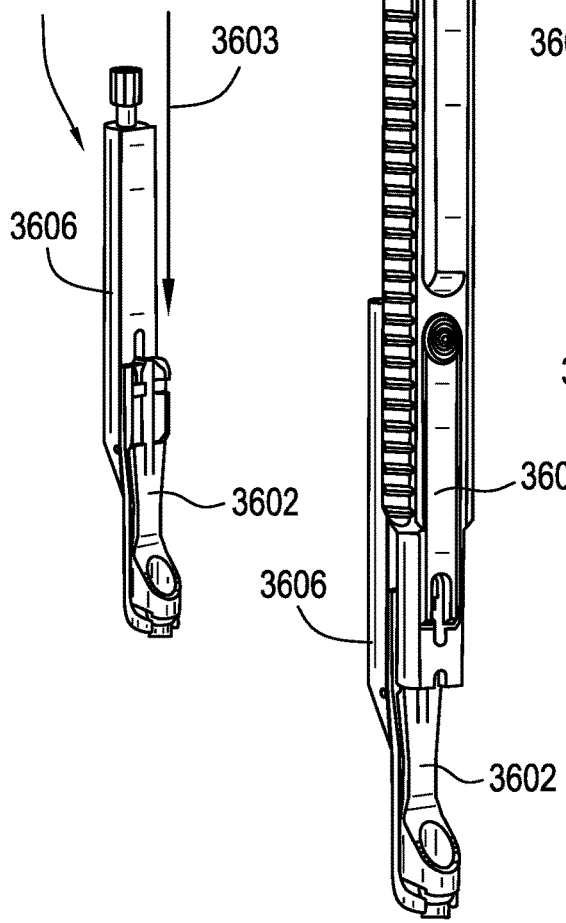
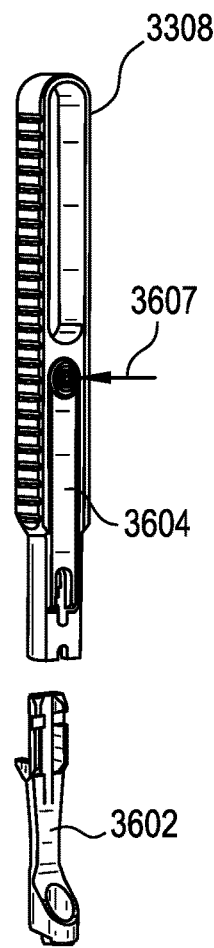

PATIENT-MOUNTED SURGICAL SUPPORT

CROSS-REFERENCE TO RELATED APPLICATIONS

This application is a continuation of U.S. patent application Ser. No. 17/168,004, filed Feb. 4, 2021. U.S. patent application Ser. No. 17/168,004 is a continuation U.S. patent application Ser. No. 16/139,409, filed Sep. 24, 2018, and now issued as U.S. Pat. No. 10,945,773. U.S. patent application Ser. No. 16/139,409 claims the benefit of U.S. Provisional Application Nos. 62/562,046 and 62/562,055, both filed on Sep. 22, 2017. The entire contents of each of these applications are incorporated herein by reference.

FIELD

This disclosure relates generally to surgical instruments, systems, and methods, and more particularly to instruments, systems, and methods for providing access to a surgical site using patient-mounted components. Such instruments, systems, and methods can be used in various procedures, e.g., orthopedic or neurologic surgical procedures such as spinal fusion surgery.

BACKGROUND

Surgical procedures are used to treat and cure a wide range of diseases, conditions, and injuries. Surgery often requires access to internal tissue through open or minimally invasive surgical procedures. The term "minimally invasive" refers to all types of minimally invasive surgical procedures, including endoscopic, laparoscopic, arthroscopic, natural orifice intraluminal, and natural orifice transluminal procedures. Minimally invasive surgery can have numerous advantages compared to traditional open surgical procedures, including reduced trauma, faster recovery, reduced risk of infection, and reduced scarring.

Whether minimally invasive or not, there are a number of surgical procedures in which it can be desirable to form a working channel in a patient to provide access to a surgical site within the patient. One such example is orthopedic or neurologic surgical procedures, including, e.g., spinal fusion procedures where it can be desirable to form a working channel through a patient's tissue to access their vertebrae and/or the intervertebral discs disposed between adjacent vertebrae.

A variety of methods for providing such a working channel are known, including various devices that are anchored to a surgical table upon which a patient is disposed, devices that penetrate tissue without being anchored to any other structure, or devices that couple to a plurality of anchors implanted in a patient's bone. In such arrangements, the devices may be inadequately supported, may undesirably move relative to a patient if the patient moves relative to the operating table or some other external structure, or may impede a surgeon or other user in performing some aspect of a procedure.

By way of example, in spinal procedures involving operation on a patient's intervertebral disc disposed between adjacent vertebrae, access to the disc space can be difficult. Prior approaches can involve performing work on intervertebral discs before implanting pedicle screws in the adjacent vertebrae. Surgery on the intervertebral disc, however, can involve removal of portions of bone from the adjacent vertebrae, which can make subsequent implanting of pedicle screws more difficult. Implanting screws before removing vertebral bone can therefore be desirable, but surgeons cannot implant the pedicle screws with receiver heads before performing intervertebral disc work because the receiver heads (and extension posts typically coupled thereto) can block access to the intervertebral disc space. As a result, surgeons often resort to inserting guidewires for the pedicle screws, bending the guidewires away from the intervertebral space to perform disc operations around the guidewires, then implanting the pedicle screws.

The advent of modular pedicle screws can allow pedicle anchors to be implanted before performing intervertebral disc operations. This is because modular pedicle screws can include a lower-profile implantable anchor that can be implanted without impeding access to, e.g., an intervertebral disc. A spinal fixation element receiver can be coupled to the anchor after implantation and completion of any intervertebral disc operation. Such anchors can also provide a rigid access point indexed to the patient's anatomy.

Accordingly, there is a need for improved access devices, systems, and methods that can streamline the instrumentation and methodology of various surgical procedures. For example, there is a need for improved access devices, systems, and methods that can utilize anchors implanted in a patient's anatomy to support surgical instruments.

SUMMARY

In some embodiments, a patient-mounted surgical support is provided that can couple to an implanted anchor and provide an adjustable and selectively lockable platform for securing other surgical instruments and/or assemblies. For example, a surgical support can be provided that can couple to a single implanted pedicle screw or other anchor and provide selective or lockable polyaxial adjustment relative thereto. Further, the surgical support can be configured to couple to another instrument or assembly, such as a tissue retractor, that can manipulate tissue to provide a working channel to a surgical site, such as a patient's intervertebral disc space. Such a support instrument can advantageously be indexed to a patient via coupling with the implanted anchor and can minimize space required to support a retractor or other instrumentation. While the instruments, devices, systems, and methods described herein can be utilized in a variety of surgical procedures, they can have particular utility in various orthopedic or neurologic surgical procedures, such as spinal operations.

In one aspect, a surgical instrument is provided that can include an elongate body and opposed projections extending laterally from a distal portion of the elongate body that can be configured to at least partially surround a shank of an implantable anchor at a position distal of a proximal head of the anchor such that a longitudinal axis of the elongate body is laterally offset from a longitudinal axis of the anchor. The instrument can also include a lock configured to exert a drag force on the head of the anchor to control polyaxial movement of the instrument relative to the anchor. Further, a proximal portion of the elongate body can be configured to receive a retractor assembly including a plurality of tissue manipulating blades and selectively lock the retractor assembly at any of a plurality of positions along a length of the proximal portion of the elongate body.

The instruments and methods described herein can have a number of additional features and/or variations, all of which are within the scope of the present disclosure. In some embodiments, for example, the lock can be configured to translate relative to the elongate body and contact an upper portion of the proximal head of the anchor. In some embodiments, the instrument can further include a biasing element disposed within a lumen of the elongate body that can be configured to urge the lock into contact with the anchor head to exert the drag force on the anchor. In certain embodiments, the instrument can also include a locking screw disposed within a lumen of the elongate body and configured to adjust the drag force exerted on the head of the anchor. Still further, the lock can include a laterally-extending ring-shaped projection at a distal end thereof that can contact the anchor head while maintaining access to a drive feature formed on a proximal end of the anchor head. In some embodiments, the lock can further include a ring-shaped driver guide pivotally coupled thereto.

In certain embodiments, the proximal portion of the elongate body can include a plurality of holes formed therein that can be configured to receive a locking pin of the retractor assembly to selectively lock the retractor assembly at any of a plurality of positions along the length of the proximal portion of the elongate body. In other embodiments, the proximal portion of the elongate body can include a ratchet configured to interface with a pawl coupled to the retractor assembly to selectively lock the retractor assembly at a plurality of positions along the proximal portion of the elongate body In some embodiments, the plurality of tissue manipulating blades can be translated laterally relative to the longitudinal axis of the elongate body. For example, in some embodiments the blades can be translated in a medial-lateral direction toward or away from one another. Moreover, in some embodiments the plurality of tissue manipulating blades can be pivoted about an axis that is transverse to the longitudinal axis of the elongate body. Such movement can include toeing, wherein a distal end of the plurality of tissue manipulating implements moves any of toward or away from one another while a distance between proximal ends of the plurality of tissue manipulating implements remains unchanged.

In another aspect, a surgical method is provided that includes positioning opposed projections of a shank extension instrument to at least partially surround a shank of an implantable anchor at a position distal of a proximal head of the anchor such that a longitudinal axis of the elongate body is laterally offset from a longitudinal axis of the anchor, as well as exerting a drag force on the head of the anchor to control polyaxial movement of the shank extension instrument relative to the anchor. The method can also include coupling a retractor assembly including a plurality of tissue manipulating implements to a proximal portion of the shank extension instrument, and retracting soft tissue by moving the plurality of tissue manipulating implements of the retractor assembly.

As with the system described above, a number of variations and additional features are possible. For example, in some embodiments exerting a drag force on the head of the anchor can include translating a lock relative to the elongate body to contact an upper portion of the proximal head of the anchor. By way of further example, in some embodiments the method can further include adjusting a position of the retractor assembly relative to the elongate body to position the plurality of tissue manipulating implements relative to tissue, as well as locking a position of the retractor assembly relative to the elongate body.

In some embodiments, retracting soft tissue by moving the plurality of tissue manipulating implements of the retractor assembly can include translating opposed implements in a medial-lateral direction. In certain embodiments, retracting soft tissue by moving the plurality of tissue manipulating implements of the retractor assembly can also and/or alternatively include toeing the opposed implements to bring distal ends thereof any of closer or father away from one another.

In some embodiments, the method can further include coupling a light to the retractor assembly to illuminate a workspace between the plurality of tissue manipulating blades. Moreover, in some embodiments the method can further include coupling the retractor assembly to an external rigid structure, such as a surgical table, etc. In certain other embodiments, however, the retractor assembly can be anchored solely to the anchor.

In some embodiments, the method can further include implanting the anchor in bone prior to positioning the opposed projections of the shank extension instrument to at least partially surround the shank of the anchor. In other embodiments, the method can include implanting the anchor in bone after positioning the opposed projections of the shank extension instrument to at least partially surround the shank of the anchor. Moreover, in some embodiments the method can include coupling a polyaxial receiver head to the proximal head of the anchor.

In another aspect, a surgical instrument assembly is provided that includes an implantable anchor having a proximal head and a distally-extending shank with a diameter smaller than a diameter of the proximal head, as well as an anchor extension. The anchor extension can include an elongate body and opposed projections extending laterally from a distal portion of the elongate body that at least partially surround the shank of the anchor at a position distal of a proximal head of the anchor such that a longitudinal axis of the elongate body is laterally offset from a longitudinal axis of the anchor. The anchor extension can also include a lock that exerts a drag force on the head of the anchor to control polyaxial movement of the extension relative to the anchor. The assembly can further include a tissue retractor coupled to a proximal portion of the anchor extension, the tissue retractor including a plurality of implements that move laterally relative to the longitudinal axis of the elongate body of the anchor extension to retract tissue.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF THE DRAWINGS

FIG. 10A is a front perspective view of another embodiment of a surgical instrument according to the teachings provided herein;

FIG. 10B is a cross-sectional view of the instrument of FIG. 10A;

FIG. 10C is a rear perspective view of the instrument of FIG. 10A;

FIG. 21 is a perspective view of an anchor extension of the instrument of FIG. 20;

FIG. 22 is a perspective view of a tissue manipulating implement of the instrument of FIG. 20;

FIG. 36A is a perspective view of a first step in a method of using a surgical instrument component removal tool;

FIG. 36B is a perspective view of a second step in a method of using the surgical instrument component removal tool of FIG. 36A;

FIG. 36C is a perspective view of a third step in a method of using the surgical instrument component removal tool of FIG. 36A; and FIG. 36D is a perspective view of a fourth step in a method of using the surgical instrument component removal tool of FIG. 36A.

DETAILED DESCRIPTION

Figure 1:
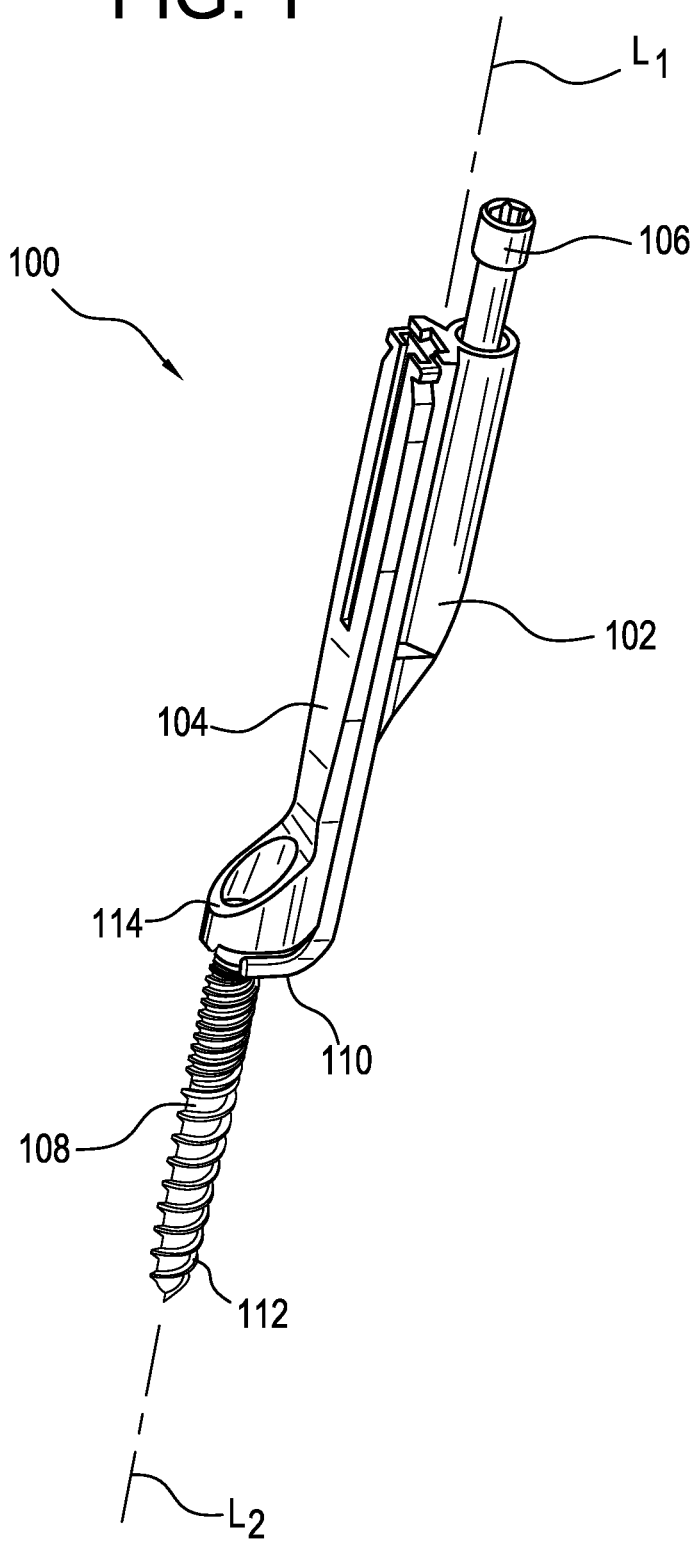
FIG. 1 is an illustration of one embodiment of a surgical instrument according to the teachings provided herein.
Figure 2A:
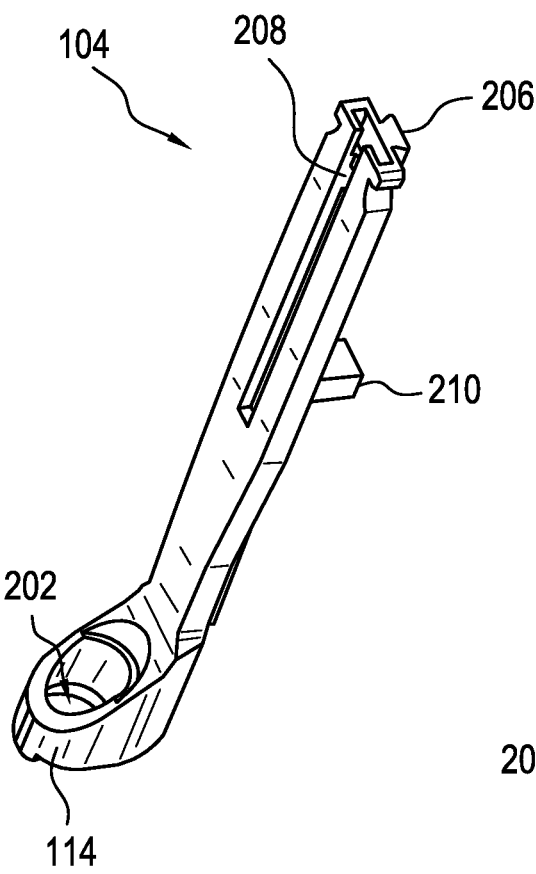
FIG. 2A is a front perspective view of a lock of the instrument of FIG. 1.
Figure 2B:
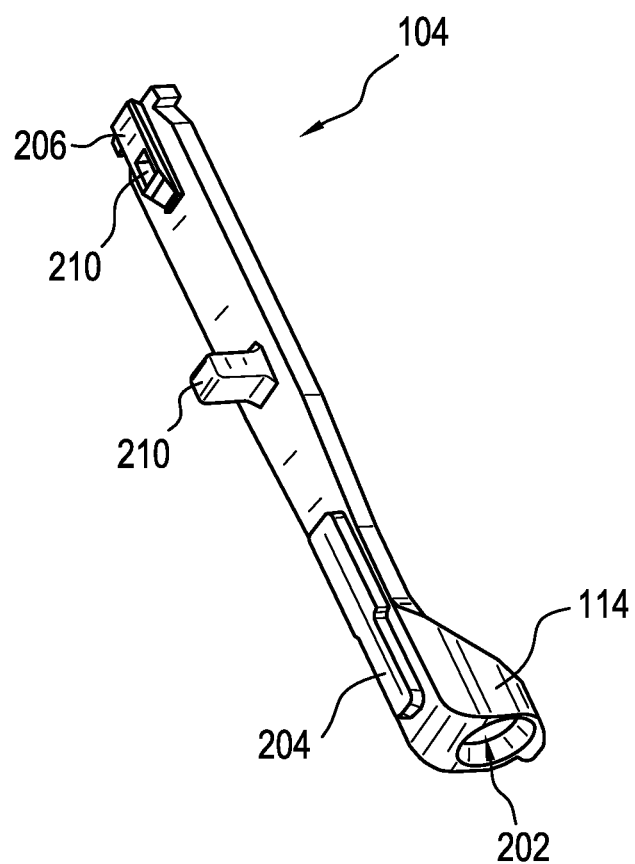
FIG. 2B is a rear perspective view of the lock of FIG. 2A.

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure.

Additionally, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape. Further, in the present disclosure, like-numbered components of the embodiments generally have similar features. Still further, sizes and shapes of the devices, and the components thereof, can depend at least on the anatomy of the subject in which the devices will be used, the size and shape of components with which the devices will be used, and the methods and procedures in which the devices will be used.

FIGS. 1-5 illustrate an exemplary surgical instrument 100 according to the teachings provided herein. The instrument 100 can be used in various surgical procedures, including spinal surgeries such as microsurgical bone resection, spinal decompression, spinal fusion, and the like. In general, the instrument 100 can include an elongate body 102, a lock body 104, and a lock actuator 106. The instrument 100 can be configured to couple to an implantable anchor 108, such as a pedicle screw or other bone screw. Other components not illustrated here can be included or coupled to the instrument 100. Such components can include, for example, any of a variety of retractor assemblies, as described herein, as well as other components, such as a camera or visualization system, and any of a variety of other surgical instruments.

An exemplary method of using the instrument 100 of FIGS. 1-5 can include any one or more of the following steps, performed in any of a variety of sequences: a) making an incision in a skin of a patient; b) percutaneously inserting through the incision an implantable anchor, such as a pedicle or other bone screw; c) coupling the instrument 100 to the implanted anchor (e.g., a pedicle anchor); d) coupling a tissue retractor to the instrument; e) providing medial-lateral retraction of tissue surrounding an incision; f) coupling an optical visualization instrument to the tissue retractor and/or instrument; g) resecting a portion of the superior articular process, and/or performing a microsurgical decompression procedure; h) extracting intervertebral disc material including removing cartilaginous material from the vertebral endplates; i) inserting an interbody device; and j) deploying a mechanism of stabilization to stabilize the intervertebral segment.

Returning to FIGS. 1-5, the elongate body 102 of the instrument 100 can include a fork 110 formed at a distal end thereof that can interface with a narrowed neck 402 of the anchor 108. The fork 110 can include opposed projections 302a, 302b that extend laterally from a distal portion of the elongate body 102 in a manner that is transverse or oblique to a longitudinal axis L3 of the elongate body. The projections 302a, 302b can define a U-shaped or otherwise open-ended recess 304 that can be sized to receive a portion of the implantable anchor 108. For example, the projections 302a, 302b can be configured to fit around a proximal portion of a bone anchor that can be part of a modular mono- or poly-axial pedicle screw. Such anchors can include a generally cylindrical distal shank portion 112 with threads for tapping into bone, as well as a narrowed neck 402 proximal of the shank portion 112 and a wider proximal head 404. The proximal head 404 can be generally spherical or semi-spherical in shape and can be configured to couple with a receiver head before or after implantation in a patient's bone. Such bone anchor assemblies are known in the art and described, for example, in U.S. application Ser. No. 15/208, 872 filed on Jul. 13, 2016 and entitled "BONE ANCHOR ASSEMBLIES AND RELATED INSTRUMENTATION" (now published as US-2018-0014858-A1), the entire contents of which are incorporated by reference herein. The size and spacing of the projections 302a, 302b can be configured such that the narrowed neck 402 fits within the recess 304 but proximal or upward movement of the elongate body 102 is prevented by interference between the projections and the wider proximal head 404.

Once the projections 302a, 302b of the fork 110 are disposed around the neck 402 of the anchor 108, friction between the elongate body and the anchor can cause a drag force to any of resist and prevent movement of the elongate body relative to the anchor. In certain embodiments, the drag force can be sufficient to prevent movement of the elongate body 102 relative to the anchor 108 in the absence of deliberate manipulating force applied, for example, by a user grasping the elongate body and adjusting its position polyaxially relative to the anchor. Such a drag force can be applied in a variety of manners. For example, in some embodiments tissue forming incision walls surrounding the anchor 108 can exert sufficient force against the fork 110 to prevent relative movement between the fork and the anchor. Such force might be an inward or compression force exerted by tissue surrounding the anchor 108, or the fork 110 can be pulled upward such that a skin surface of the patient is disposed below the fork and exerts an upward force on the fork. As another example, the anchor 108 can be tightened to compress the fork 110 between the head portion 404 of the anchor and a bone surface.

In addition or alternatively, the instrument can include a lock configured to exert a drag force on the head of the anchor to control polyaxial movement of the instrument 100 relative to the anchor 108. As shown in FIGS. 1-5, such a lock can include a lock body 104 that is coupled to the elongate body 102 and translatable relative thereto along the longitudinal axis L3 of the elongate body. The lock body 104 can have a generally elongate shape to facilitate coupling with and translating or sliding along or relative to the elongate body 102. The lock body 104 can further include a laterally-extending ring-shaped projection 114 at a distal end thereof that can be configured to contact the proximal head 404 of the anchor 108 and exert a drag force thereon. A lumen 202 defined by the ring-shaped projection 114 can maintain access to a drive feature 502 formed on a proximal end of the head 404 of the anchor 108. This lumen, in combination with the lateral extension of the projection 114 and fork 110 can orient the instrument 100 such that a longitudinal axis $L_1$ of the instrument is laterally offset or non-coaxial with a longitudinal axis L2 of the anchor 108. Such a configuration can allow a driver or other instrument to access the drive feature 502 of the anchor 108 even when the instrument 100 is coupled thereto. This can enable flexibility to implant the anchor 108 any of before and after coupling the instrument 100 thereto.

The lock body 104 can also include any of a variety of features to facilitate slidable coupling with the elongate body 102. For example, the lock body 104 can include indexing projections 204, 206 that can be configured to be received within longitudinally-extending slot 306 formed in the elongate body. The projections 204, 206 and slot 306 can have any of a variety of complementary shapes and, in some embodiments, can include one or more angled surfaces, e.g., dovetails, etc., that can permit longitudinal or axial translation while preventing lateral or radial separation of the components. The slot 306 can also include one or more widened portions 308, 310 such that the lock body 104 can be translated to a position where lateral or radial separation of the lock body and the elongate body 102 is permitted.

The lock body 104 can also include a slot 208 formed therein that can receive a second lock 504. The second lock 504 can be configured to prevent the lock body 104 from being translated to the above-described position relative to the elongate body 102 wherein lateral or radial separation of the lock body from the elongate body is permitted. For example, the second lock 504 can include a projection 506 that when assembled, can extend through a passage 210 formed in the lock body 104 and into a bore 312 formed in the elongate body 102. Proximal translation of the lock body 104 can therefore be limited by interaction of the projection 506 with a proximal sidewall of the bore 312 at a position wherein the projections 204, 206 of the lock body 104 are not aligned with the widened portions 308, 310 of the slot 306 in the elongate body. Removal of the second lock 504, however, can allow unrestricted proximal translation of the lock body 104 relative to the elongate body 104 to a position where the projections 204, 206 align with the widened portions 308, 310 of the slot 306 and separation of the two components is possible.

Figure 4:
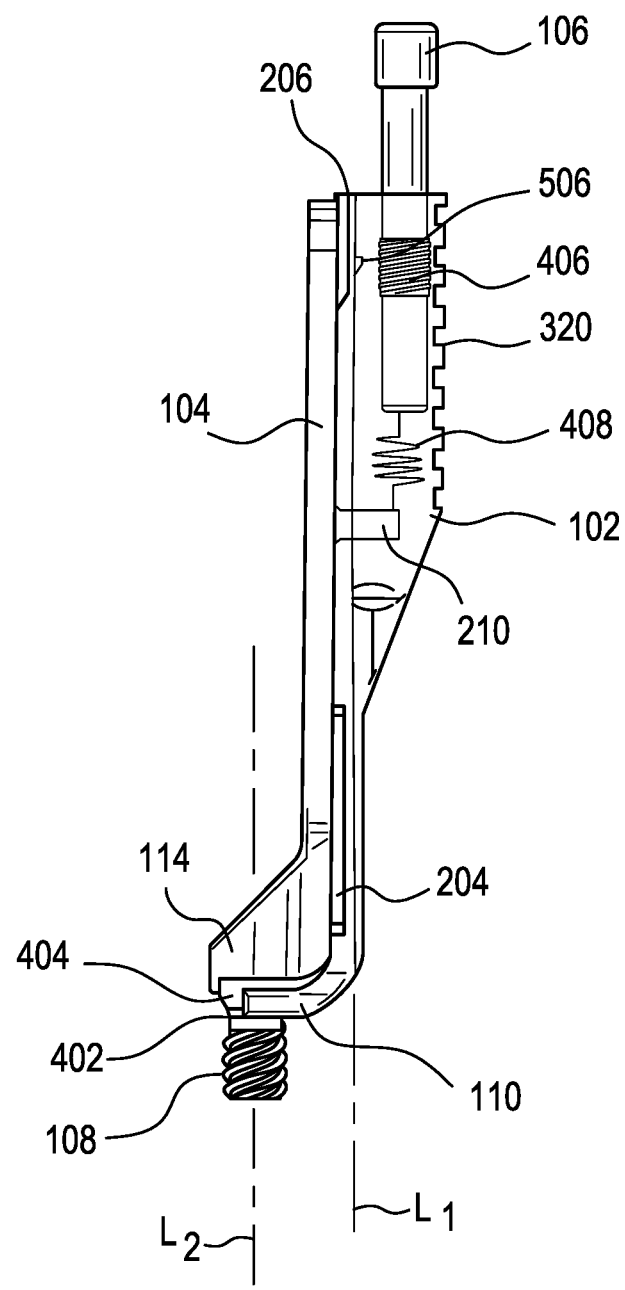
FIG. 4 is a partially-transparent side view of the instrument of FIG. 1 coupled to an implantable anchor.
Figure 5:
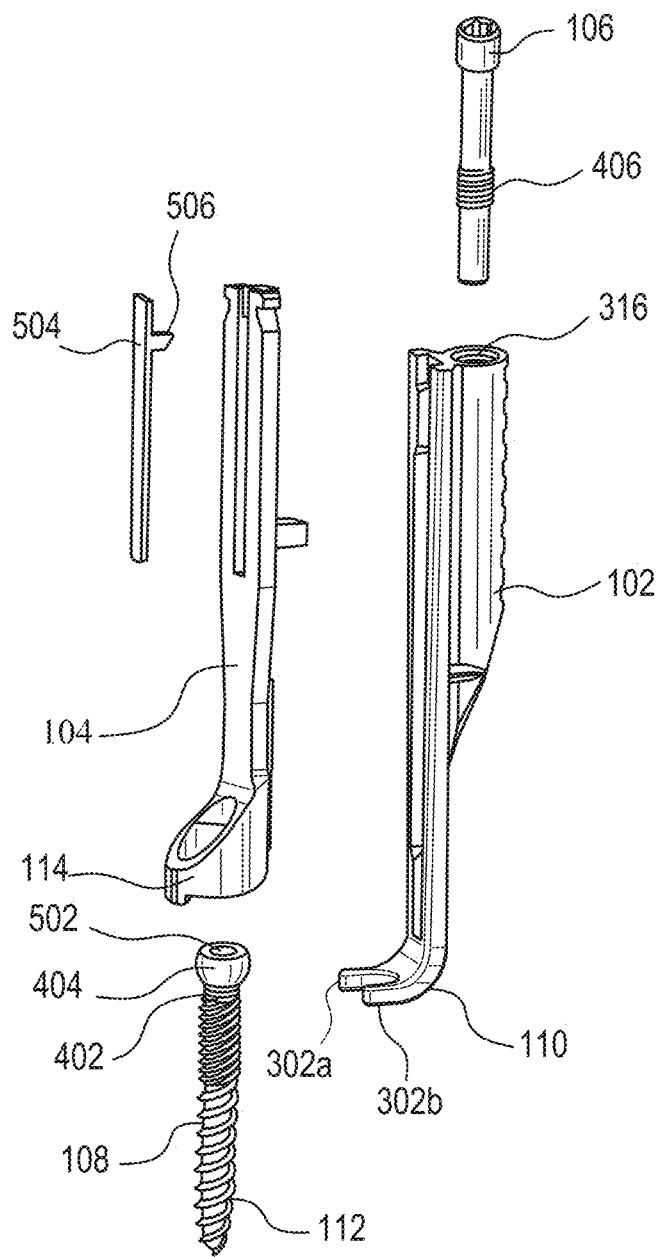
FIG. 5 is an exploded view of the instrument of FIG. 1.

As noted above, the lock body 104 can impart a drag force on the proximal head 404 of the anchor 108 to control (e.g., selectively permit or prevent, with varying levels of manipulating force required to achieve) polyaxial movement of the instrument 100 relative to the anchor 108. The level of force imparted by the lock body 104 can be controlled by a locking actuator 106, e.g., a locking screw in the illustrated embodiment. The locking screw 106 can be disposed within a lumen 314 of the elongate body 102, for example, threads 406 formed on the locking screw 106 can engage complementary threads 316 formed on an inner surface of the lumen 314. Distal advancement of the screw 106 can exert a distal force on the lock body 104 via a protrusion 210 extending into a bore 318 formed in the elongate body 102. In some embodiments, a distal portion of the locking screw or other actuator 106 can directly contact the protrusion 210. In other embodiments, and as illustrated in FIG. 4 for example, a biasing element 408 can be disposed between the screw 106 and the protrusion 210. The biasing element 408, which can be, e.g., a coil or other compression spring, can impart a desired drag force that can semi-rigidly maintain a position of the instrument 100 relative to the anchor 108 while continuing to permit polyaxial movement of the instrument if, for example, a user overcomes the drag force. When desired, a complete lockout of all relative movement between the instrument and the anchor can be achieved by distal advancement of the locking screw or other actuator 106.

In some embodiments, the instrument 100 can be configured to permit attachment of a modular receiver head to the proximal head 404 of the anchor 108 without decoupling of the anchor and the instrument 100. For example, in the illustrated embodiment the locking actuator 106 can be proximally retracted at least partially and can be removed entirely to remove the drag force imparted on the anchor 108 by the lock body 104. Further, the second lock 504 can be removed to allow the lock body 104 to be translated proximally and subsequently decoupled from the elongate body 102. An instrument for assisting in removal of the lock body 104 is illustrated in FIGS. 36A-36D, described in more detail below. A modular receiver head (not shown) can then be coupled to the proximal head 404 of the anchor 108. The elongate body 102 can be left in place, as it is offset from the anchor 108 by the laterally-extending projections 302a, 302b of the fork 110 and because the projections 302a, 302b disposed below the proximal head 404 will not interfere with coupling a receiver head to the proximal head of the anchor 108. Further, and as noted above, in some embodiments a position of the elongate body 102 relative to the anchor 108 can continue to be maintained even after the lock body 104 is removed by, for example, force applied by tissue surrounding the anchor and elongate body. Still further, in some embodiments the elongate body 102 or other component coupled thereto can be coupled to an external rigid structure, such as a surgical table, etc. Such an external rigid structure can aid in maintaining a position of the elongate body 102 even after removal of the lock body 104.

Figure 3A:
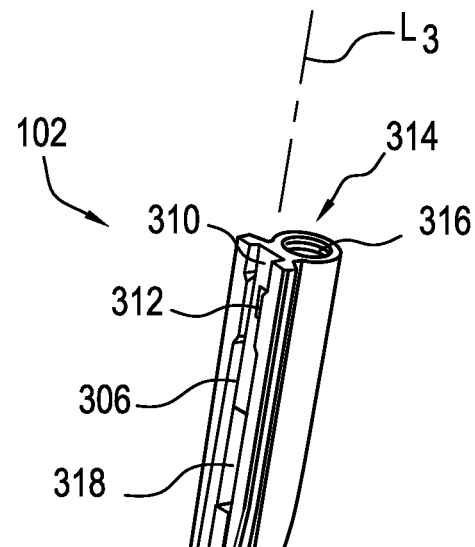
FIG. 3A is a front perspective view of an elongate body of the instrument of FIG. 1.
Figure 3B:
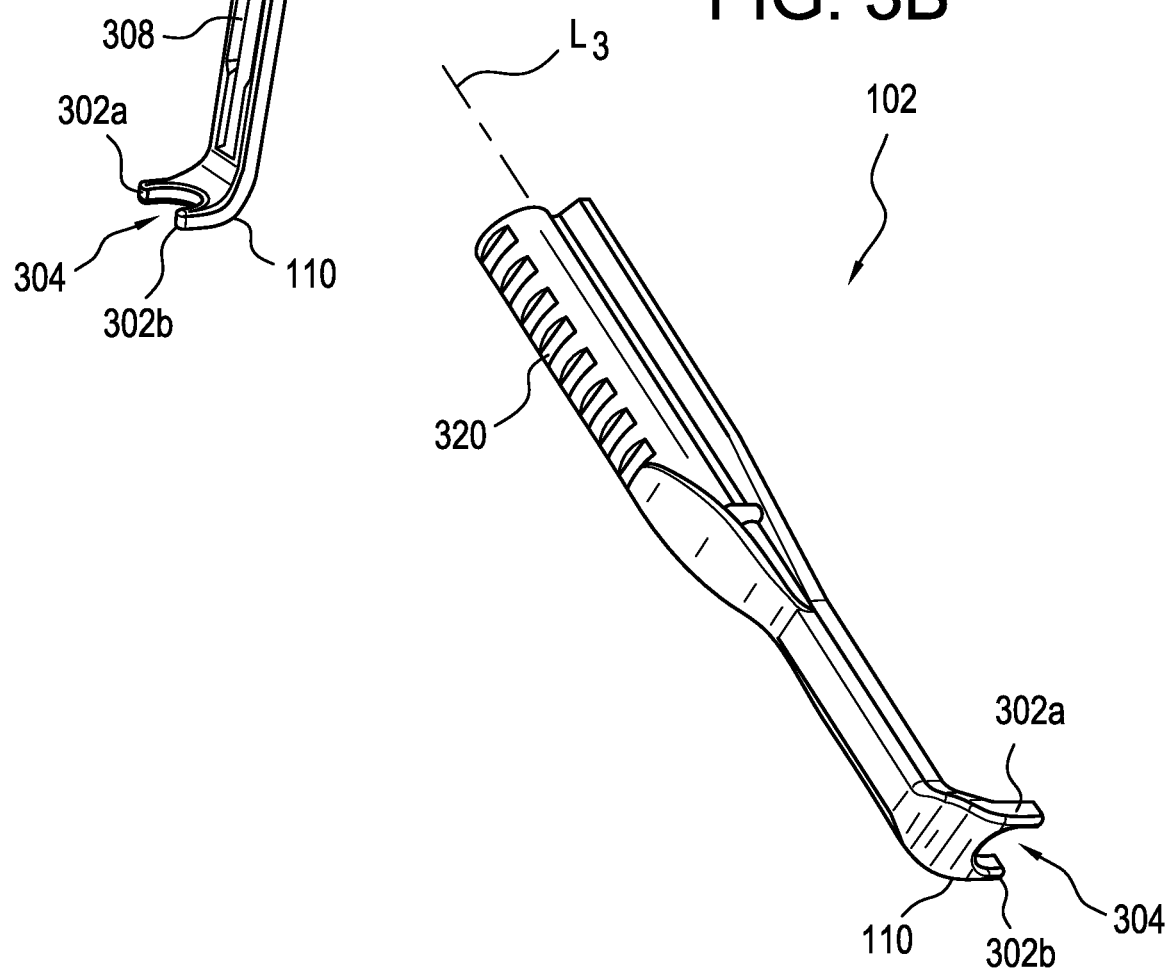
FIG. 3B is a rear perspective view of the elongate body of FIG. 3A.

The instrument 100 can be configured to couple with a retractor assembly, as described in more detail below. The retractor assembly can include a plurality of tissue manipulating implements that can be used to, for example, widen an incision formed in a patient's skin and tissue to enable better access to a surgical site. In some embodiments, the retractor assembly can couple to a proximal portion of the elongate body 102 and can selectively lock at any of a plurality of positions along a length of the proximal portion of the elongate body. For example, and as shown in FIGS. 3B and 4, the elongate body 102 can include a plurality of notches 320 formed along a length of a proximal portion thereof. The series of notches 320 can serve as a ratchet that can interface with a pawl-like feature of the retractor assembly, such as a protrusion or other portion of the assembly, to secure the assembly against movement along the longitudinal axis L3 of the elongate body 102.

Accordingly, the above described support instrument 100 can provide a platform for mounting a retractor assembly that is anchored to a single implanted bone screw or other anchor. This can provide a number of advantages. For example, it can be advantageous to utilize a support that is anchored to a patient's body, as opposed to an external structure, such as a surgical table, etc. For example, anchoring relative to a patient's body can provide an advantage by maintaining a relative position between an access device and a patient even if a patient moves during a procedure. Moreover, it can be advantageous to anchor to a single bone screw or other anchor (e.g., as opposed to constructs that span across multiple implanted anchors), as this can reduce the footprint of instrumentation and can allow greater working space for other implements employed in a procedure. In some embodiments, however, it can be possible to also anchor the instruments and assemblies described herein to an external structure, such as a surgical table, etc. In some embodiments where external fixation is employed, locking against movement relative to an implanted anchor can be avoided such that some adjustment relative to an implanted anchor is possible in case of patient movement, etc.

Figure 6A:
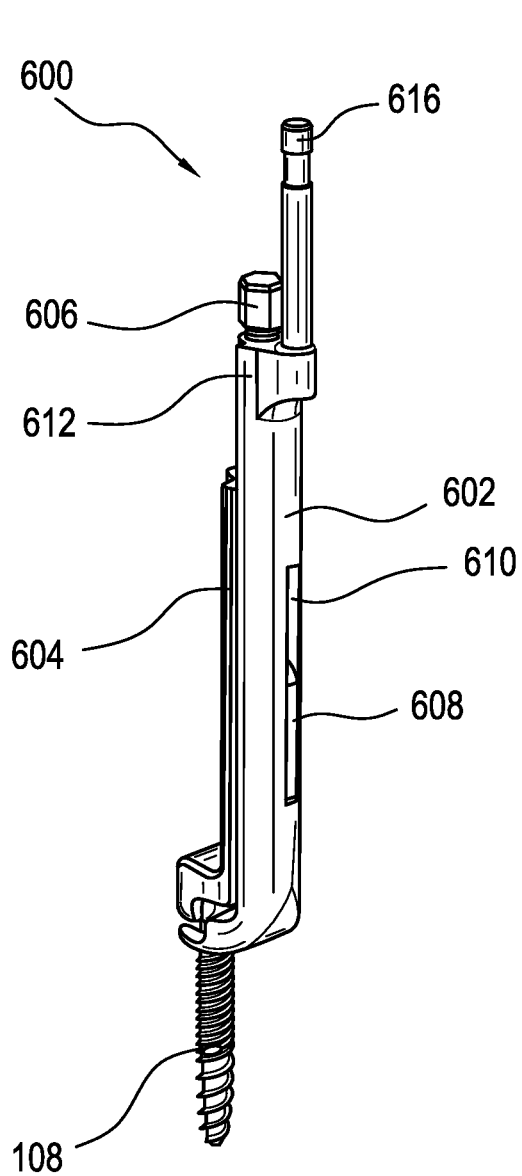
FIG. 6A is a rear perspective view of another embodiment of an instrument according to the teachings provided herein.
Figure 6B:
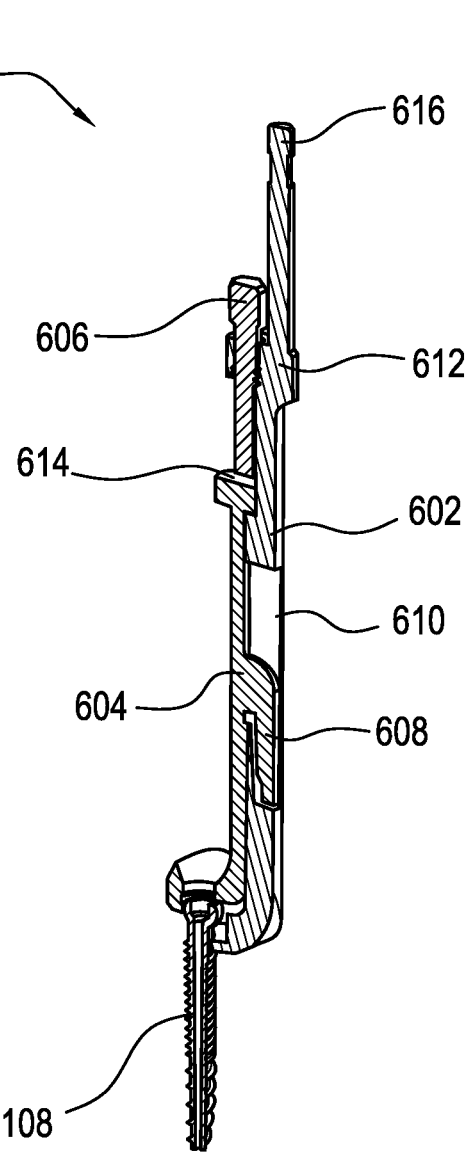
FIG. 6B is a rear perspective cross-sectional view of the instrument of FIG. 6A.

A variety of alternative embodiments of support instruments are within the scope of the present disclosure. For example, FIGS. 6A-11 illustrate various exemplary alternative embodiments of a surgical support instrument similar to the instrument 100. The instrument 600 of FIGS. 6A and 6B, for example, is coupled to the anchor 108 and includes an alternative configuration of an elongate body 602 and lock body 604. For example, the lock body 604 can include a hook-shaped projection 608 that can be disposed within a slot 610 formed in the elongate body 602. The projection 608 and slot 610 are an alternative geometry that can serve a similar purpose as the projections 204, 206 and slot 306 described above. Also visible in FIGS. 6A and 6B is an alternative geometry for the locking screw 606, which threads through a proximal portion 612 of the elongate body 602 and directly contacts a proximal end 614 of the lock body 604. Further, the elongate body 602 includes a proximally extending post 616 that can be utilized to couple the instrument 600 to, for example, a retractor assembly or external fixation structure, as described herein.

Figure 7:
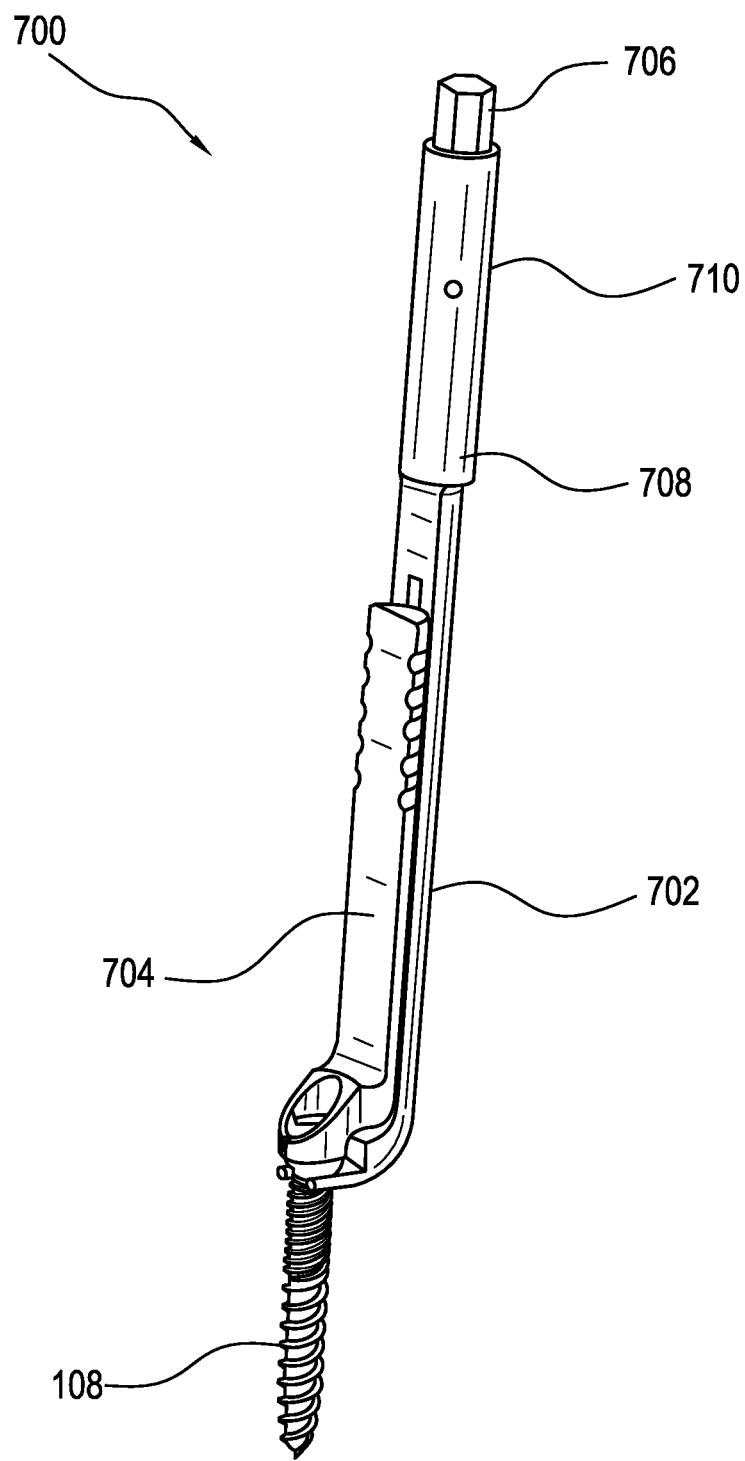
FIG. 7 is a front perspective view of another embodiment of a surgical instrument coupled to an implantable anchor.

FIG. 7 illustrates another embodiment of an instrument 700 coupled to the anchor 108. The instrument 700 includes an elongate body 702, lock body 704, and lock actuator 706 for selectively controlling polyaxial movement of the instrument relative to the anchor. The elongate body 702 includes an extended proximal portion 708 that increases a height of the elongate body to provide additional mounting options for a retractor assembly to be coupled thereto. Any desired length of the elongate body 702 and proximal portion 708 thereof is possible, and a length of the lock actuator 706 can be adjusted accordingly to maintain operability of the instrument. Moreover, the proximal portion 708 can include a plurality of holes 710 formed therein that can be used to lock a position of a retractor assembly relative thereto. For example, one or more of the holes 710 can receive one or more locking pins coupled to the retractor assembly to achieve a lock between the components, similar to the ratchet-and-pawl configuration described above. Alternatively, a retractor assembly or other implement can couple to the elongate body proximal portion 708 in another manner, for example by clamping around the cylindrical proximal portion of the elongate body with sufficient force to prevent relative movement between the two components.

Figure 8A:
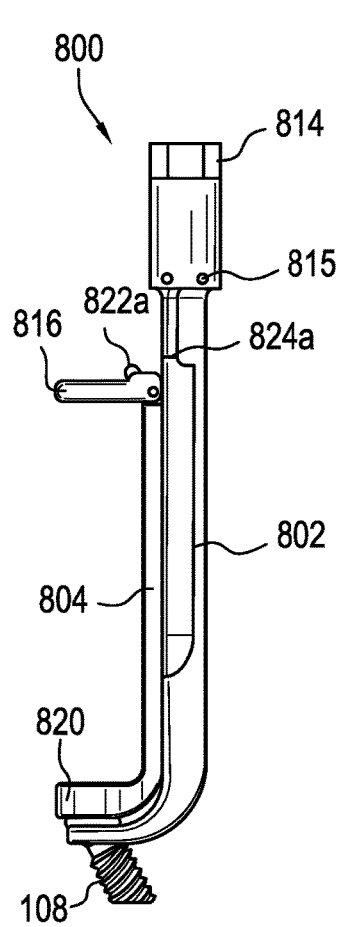
FIG. 8A is a side view of another embodiment of a surgical instrument coupled to an implantable anchor.
Figure 8B:
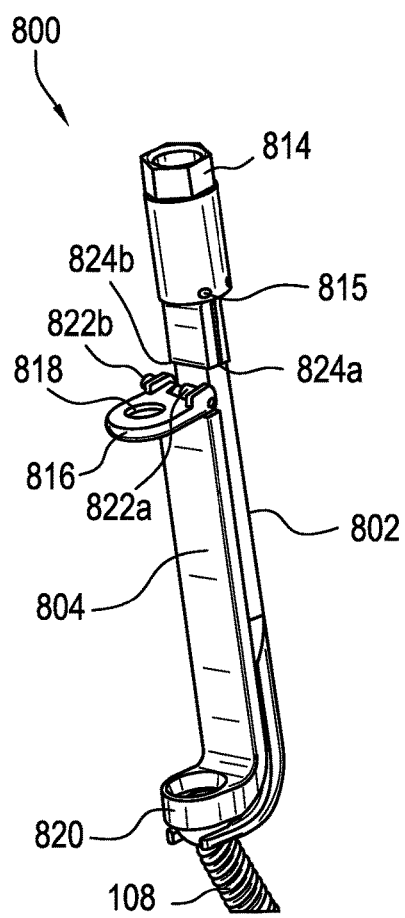
FIG. 8B is a front perspective view of the instrument of FIG. 8A.
Figure 8C:
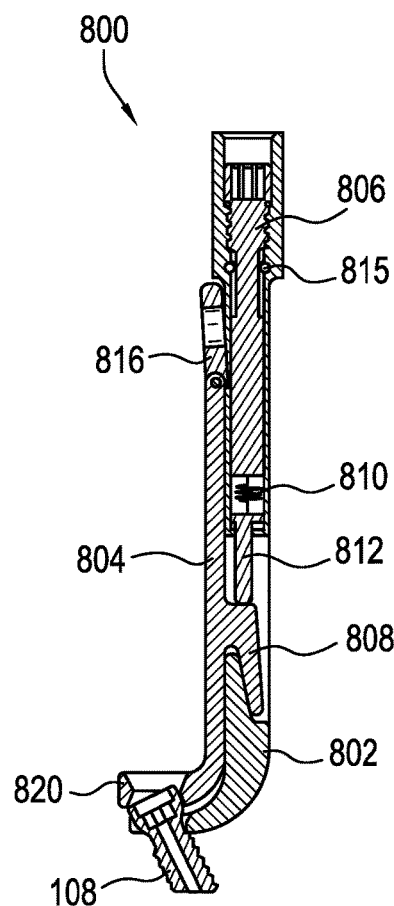
FIG. 8C is a partially-transparent side view of the instrument of FIG. 8A.

FIGS. 8A-8C illustrate another embodiment of an instrument 800 that can couple to the anchor 108 and includes an alternative configuration of an elongate body 802 and a lock body 804. For example, the lock body 804 can include a hook-shaped projection 808 disposed within a slot formed in the elongate body 802, similar to the instrument 600 described above. Moreover, a proximal surface of the hook-shaped projection 808 can be used to control the drag force imparted on the anchor 108 by the lock body 804 via the lock actuator 806. In the illustrated embodiment, the lock actuator includes a screw 806 threaded into a proximal portion of the elongate body 802, as well as a biasing element 810 and an intermediate member 812 that extends between the projection 808 and the biasing element 810.

A proximal portion of the elongate body 802 can include one or more holes 815 formed therein that can receive, for example, a locking pin from a retractor assembly or other implement to be coupled to the instrument 800, similar to the holes 710 described above. The proximal portion of the elongate body can also include one or more tool-interfacing surfaces 814, such as one or more pairs of opposed planar surfaces, that can be utilized to prevent rotation of the elongate body 802 as a torque is applied to the locking screw 806. For example, a wrench or other tool can be utilized to immobilize the elongate body 802 or apply a counter torque thereto as the locking screw 806 is rotated to engage or disengage locking of the instrument 800 relative to the anchor 108.

Still further, the lock body 804 of the instrument 800 can include a driver guide 816 coupled thereto. In the illustrated embodiment, the driver guide 816 is a ring-shaped member pivotably coupled to a proximal end of the lock body 804. The driver guide 816 can be pivoted or rotated between a first configuration, as shown in FIGS. 8A and 8B, and a second configuration, as shown in FIG. 8C. In the first configuration, the driver guide extends laterally from the elongate body 802 and lock body 804 such that an inner lumen 818 defined by the guide is aligned with an inner lumen of the ring-shaped projection 820 of the lock body 804. In the second configuration, the driver guide 816 is aligned with the lock body 804 and lays flush against the elongate body 802, thereby clearing the space above the anchor 108 and ring-shaped projection 820. In some embodiments, the driver guide 816 can include one or more retention features, such as protrusions 822a, 822b that can interface with complementary features, such as recesses 824a, 824b formed on the elongate body 802, to maintain the driver guide 816 in the second configuration of FIG. 8C and prevent it from inadvertently falling into the first configuration of FIGS. 8A and 8B.

Figure 9A:
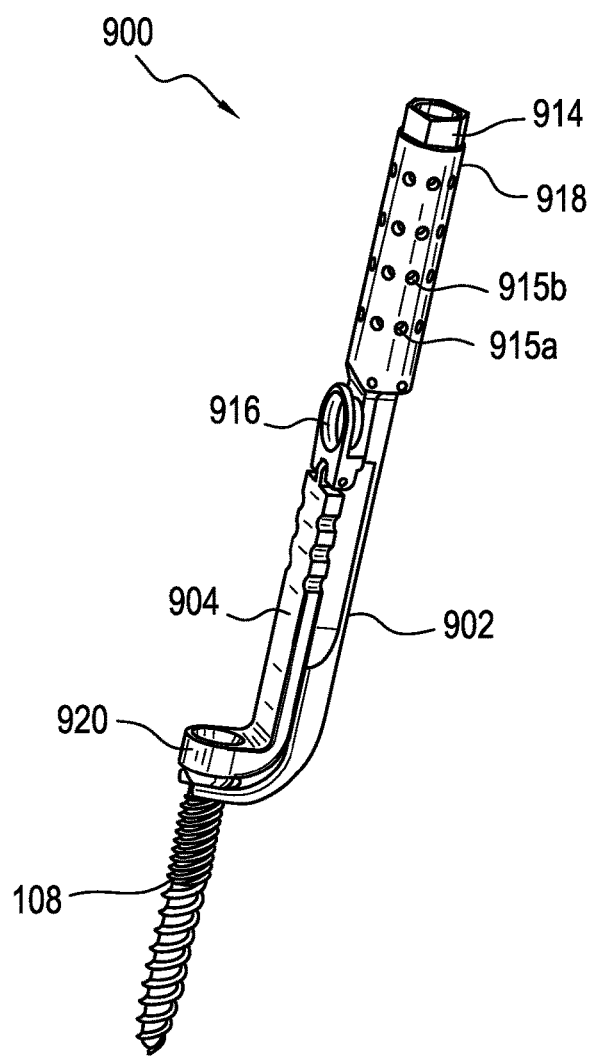
FIG. 9A is a front perspective view of another embodiment of a surgical instrument according to the teachings provided herein.
Figure 9B:
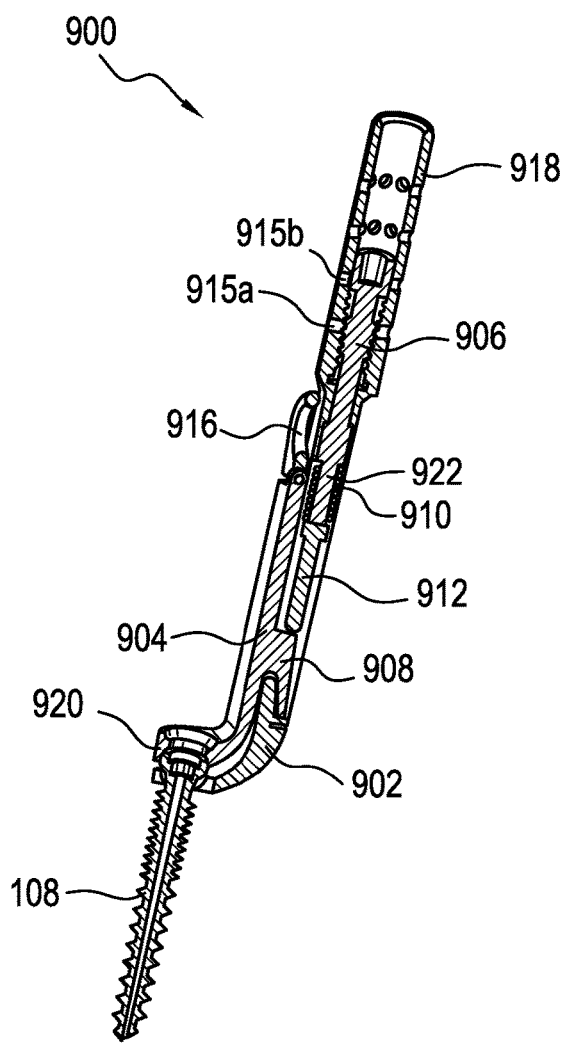
FIG. 9B is a cross-sectional view of the instrument of FIG. 9A.

FIGS. 9A and 9B illustrate a similar instrument 900 that includes an elongated proximal portion 918 have a plurality of holes 915a, 915b formed therein both around a circumference thereof and along a length thereof. The holes 915 can be configured to receive one or more locking pins of a retractor assembly or other surgical implement that can couple to the instrument 900 in order to lock any of a rotational and longitudinal position of the implement relative to the instrument. The instrument 900 also includes an alternative locking actuator that includes a screw 906 with a distal post 922 that can extend into an inner lumen of a compression spring biasing element 910 and, when advanced distally to a sufficient extent, can directly contact the intermediate member 912, as shown in FIG. 9B. When not in contact with the intermediate member 912 to directly impart force thereto, the post can aid in preventing buckling of the compression spring 910.

FIGS. 10A-10C illustrate still another embodiment of an instrument 1000 that includes an elongate body 1002, a two-part lock body 1004, 1005, and a locking actuator 1006. The elongate body 1002 is similar in configuration to the embodiments described above, including a proximal portion 1018 with a plurality of sets of holes 1015a, 1015b distributed along a length thereof that can be utilized to lock a retractor assembly or other implement at a particular position along a length of the elongate body 1002. The elongate body 1002 also includes a slot 1020 formed in a distal portion thereof. Portions of the distal lock body 1004 and proximal lock body 1005 are disposed within the slot 1020 and a biasing element 1010, such as a compression spring, can be disposed therebetween to urge the proximal lock body proximally and the distal lock body distally. Movement of the lock bodies 1004, 1005 can be limited by proximal and distal ends of the slot 1020 and the biasing element can function to exert at least a minimal drag force on an anchor 108 via the distal lock body 1004. Additional drag force, up to and including complete lockout against relative movement between the instrument 1000 and an anchor 108, can be achieved by rotating the screw 1006 to distally advance it relative to the elongate body 1002 and urge the proximal lock body 1005 distally toward the distal lock body 1004.

The proximal and distal lock bodies 1004, 1005 can include one or more complementary slots 1022 and projections (not visible) to join the lock bodies together and prevent undesirable separation or movement other than translation relative to one another along a longitudinal axis $L_1$ of the instrument. Moreover, the proximal lock body 1005 can include a pivoting driver guide 1016, similar to the above-described driver guide 816. In the illustrated embodiment, however, a further retention feature in the form of a slot 1024 is formed on a distal end of the driver guide and can be configured to interface with a projection 1026 formed on the elongate body 1002 when the driver guide is retracted toward the elongate body to prevent its inadvertent movement away from the elongate body. The retention features 1024, 1026 can be additional to, or in place or, projection features 1028 formed at an opposite end of the driver guide and configured to interface with ridge 1030 formed on the elongate body. Moreover, in the illustrated embodiment the ridge 1030 extends for a distance along the elongate body to allow the projection feature 1028 to translate relative to the elongate body along with the proximal lock body 1005.

Figure 11:
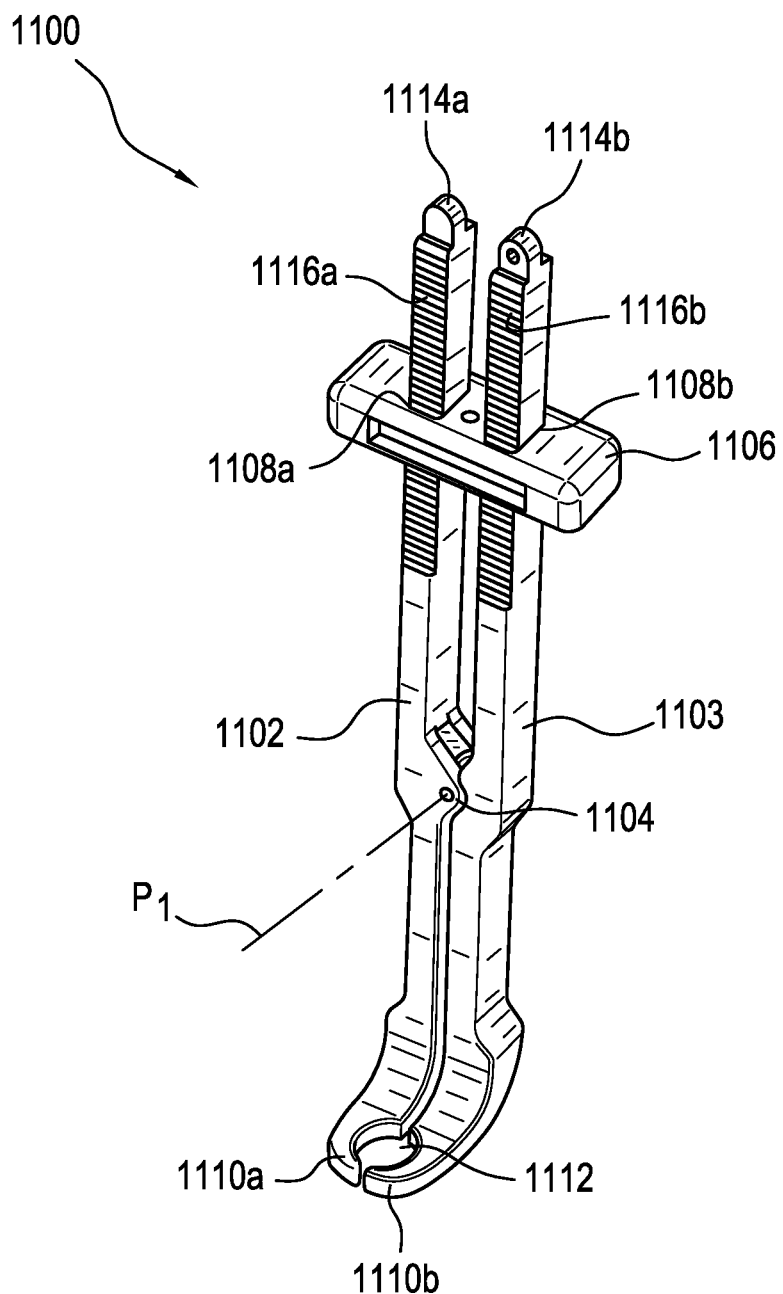
FIG. 11 is a front perspective view of another embodiment of a surgical instrument according to the teachings provided herein.

FIG. 11 illustrates still another embodiment of a support instrument 1100 configured to couple to an anchor 108. The instrument 1100 includes first and second opposed elongate bodies 1102, 1103 that are pivotably coupled to one another at hinge 1104 and therefore rotate relative to one another about an axis $P_1$. The instrument 1100 also includes a lock 1106 that includes first and second lumens 1108a, 1108b configured to receive proximal portions of each elongate bodies 1102, 1103. The lumens 1108a, 1108b can have a fixed size and position relative to one another, such that when assembled over the proximal ends of the elongate bodies 1102, 1103 the lock 1106 can maintain a position of the elongate bodies relative to one another.

A distal portion of each elongate body 1102, 1103 can include a laterally-extending projection 1110a, 1110b that can form a semi-circular shape such that the two elongate bodies 1102, 1103, when positioned adjacent to one another, define a circular recess 1112 between the projections. Accordingly, the instrument 1100 can be used by separating the lock 1106 from the elongate bodies 1102, 1103 and bringing proximal ends 1114a, 1114b toward one another. Such motion can cause rotating of the elongate bodies 1102, 1103 about the pivot 1104, thereby moving the distal projections 1110a, 1110b away from one another. The instrument 1100 can then be passed down over a proximal head 404 of an anchor 108 or laterally over a shank 112 or neck 402 underneath the proximal head 404. The proximal ends 1114a, 1114b of the elongate bodies 1102, 1103 can be moved away from one another to cause the distal projections 1110a, 1110b to move toward one another and abut against the anchor 108. Imparting sufficient force to the proximal ends (urging them away from one another) can clamp the anchor 108 with sufficient force to prevent relative movement between the instrument 1100 and the anchor 108.

A position of the instrument 1100 relative to the anchor 108 can be locked by passing the lock 1106 distally over the proximal ends 1114a, 1114b of the elongate bodies 1102, 1103 such that the elongate body 1102 is received within the lumen 1108a and the elongate body 1103 is received within the lumen 1108b. Because the sizes of the elongate bodies and the lumens of the lock are complementary, and because the lumens are fixed relative to one another on the lock 1106, the lock can maintain the relative positioning of the elongate bodies 1102, 1103 and prevent separation of the distal projections 1110a, 1110b.

Moreover, the lock 1106 can include one or more pawls, protrusions, or other features (not visible) that can interact with a series of notches, teeth, shelves, or other recesses 1116a, 1116b formed on each elongate body 1102, 1103 to set and maintain a desired height of the lock 1106 relative to the elongate bodies. A retractor assembly or other implement can then be coupled to the lock 1106 or the lock can be eliminated and the assembly can include the correctly spaced and sized lumens to directly interface with the elongate bodies 1102, 1103.

Adjusting a position of the lock 1106 along a length of the elongate bodies 1102, 1103 can, in some embodiments, not influence the clamping force maintained by the lock. For example, if sufficient clamping is achieved when the proximal portions 1114a, 1114b of the elongate bodies 1102, 1103 are parallel, the lock 1106 can exert and maintain a same clamping force at any position along the series of recesses 1116a, 1116b. Adjusting the positioning of the lock 1106 (or retractor assembly include lumens like the lock 1106) along the elongate bodies 1102, 1103 can serve to set a height of any retractor assembly or other implement that couples to the lock 1106.

In one embodiment, a user can place the distal projections 1110a, 1110b of the instrument 1100 around a cylindrical shank or neck of an anchor 108 and urge the proximal ends of the elongate bodies 1102, 1103 away from one another to secure the instrument to the anchor. The user can then couple a retractor assembly to the elongate bodies 1102, 1103 by passing the elongate bodies through lumens formed in the retractor assembly (or coupling the retractor assembly to the lock 1106 and coupling the lock to the elongate bodies). The user can then push the retractor down toward the patient's tissue causing it to slide distally along the elongate bodies 1102, 1103 until the retractor abuts against the patient's tissue. At such a point, the rigid positioning of the lumens receiving the elongate bodies 1102, 1103 can maintain their relative positioning and upward or proximal force imparted to the elongate bodies by the retractor assembly being in contact with the patient's tissue can secure the distal projections against, for example, the underside of a proximal head 404 of an anchor 108, thereby stabilizing the instrument's position.

As noted above, the various support instrument embodiments described above can be configured to couple with or receive a retractor assembly that can include a plurality of tissue manipulating implements. FIGS. 12-17B illustrate various embodiments of retractor assemblies that can be utilized in combination with the support instruments described herein. Further details on retractor assemblies can be found in U.S. application Ser. No. 16/139,434, entitled "PATIENT-MOUNTED SURGICAL RETRACTOR," filed on Sep. 24, 2018 (now published as US-2019-0090864-A1), as well as U.S. Pat. No. 7,491,168. The entire contents of these applications and patents are incorporated by reference herein.

FIGS. 12-16 illustrate a first embodiment of a retractor assembly 1200 that can couple to, for example, the surgical support instrument 100 described above. The retractor 1200 can include a plurality of tissue manipulating implements, such as tissue manipulating blades 1202, 1204. The tissue manipulating implements or blades 1202, 1204 can have any of a variety of shapes and sizes. For example, the tissue manipulating blades 1202, 1204 can have a variety of heights to extend to various depths below a patient's skin surface and to various heights above the skin surface. Further, in some embodiments a height of any of the blades 1202, 1204 can be adjustable, e.g., in an embodiment where a blade includes an inner component and an outer component configured to translate relative to one another to vary the amount by which they overlap and an overall length of the two components together. The blades 1202, 1204 can also have any of a variety of widths, shapes, and curves. For example, in some embodiments the blades can be planar, while in other embodiments, such as the illustrated embodiment, the blades can have a semi-circular curve extending along a length thereof.

The tissue manipulating implements or blades 1202, 1204 can each be coupled to a housing 1206, 1208 that can be coupled to a rack 1210. The implements 1202, 1204 can be arranged opposite one another such that they can be translated any of toward and away from one another to perform tissue retraction. In addition, other forms of movement of the implements 1202, 1204 are also possible. For example, in some embodiments the implements 1202, 1204 can be toed toward or away from one another. Toeing can involve pivoting the implements such that distal ends thereof move any of toward and away from one another while a distance between proximal ends of the implements remains unchanged.

Figure 12:
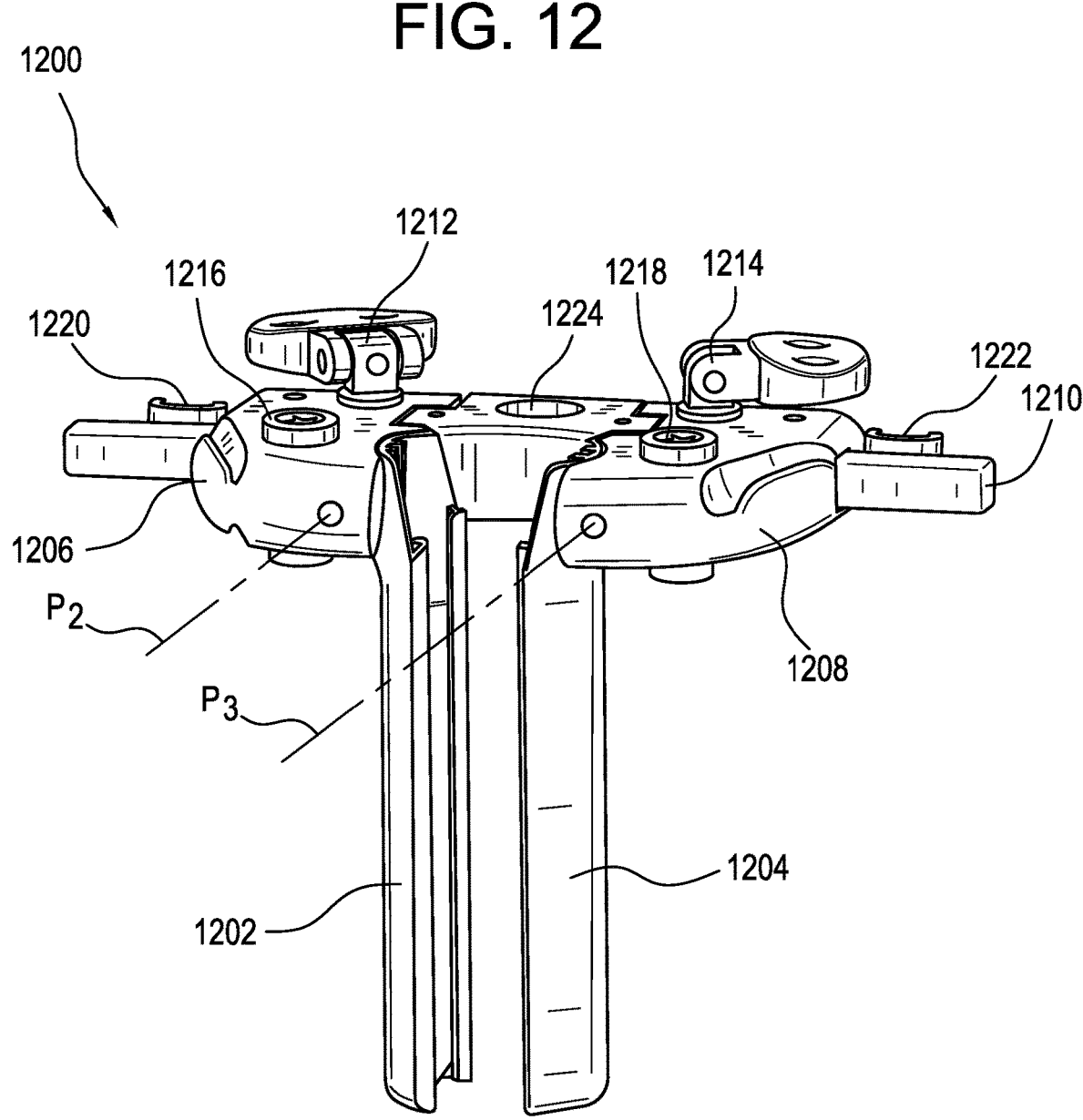
FIG. 12 is a front perspective view of one embodiment of a retractor assembly.

The various movements of the implements or blades 1202, 1204 can be controlled by any of a variety of actuators. For example, thumbwheel actuators 1212, 1214 can be rotated to control translation of the implements 1202, 1204 toward or away from one another by moving the housings 1206, 1208 along the rack 1210 via, e.g., a cog or gear coupled to each actuator 1212, 1214 within each respective housing. Moreover, in embodiments capable of toeing opposed implements 1202, 1204 relative to one another, screw actuators 1216, 1218 can be included in the housings to control pivoting of the implements or blades 1202, 1204 about axes $P_2$, $P_3$, respectively. The retractor assembly 1200 can also include features to facilitate resetting a position of the implements 1202, 1204, such as releases 1220, 1222 that can disengage the actuators 1212, 1214 from the rack 1210 and allow the housings 1206, 1208 to be rapidly slid along the rack, e.g., from a position at an end of the rack to a central or home position, as shown in FIG. 12.

A central portion of the rack 1210 can include a complete or partial through-hole or recess 1224 formed therein that can be configured to be disposed around a proximal portion of a support instrument, e.g., the proximal portion 918 of the instrument 900 described above and shown in FIGS. 13A-16. Using any of a variety of locking mechanisms, such as those described herein (e.g., movable pawls or locking pins), the retractor 1200 can be selectively locked to a support instrument at any of a particular position along a length of the support instrument and a rotational orientation relative thereto.

Figure 13A:
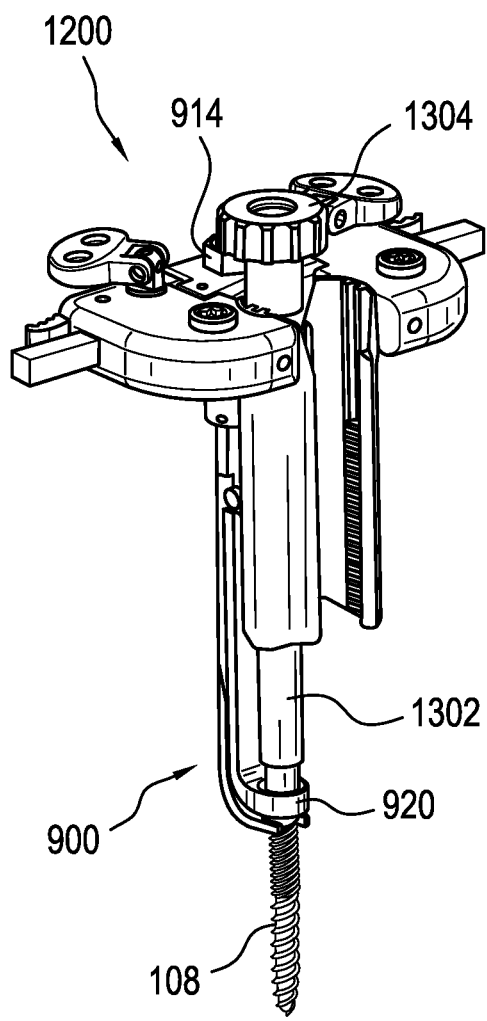
FIG. 13A is a front perspective view of one embodiment of a surgical instrument assembly including the extension of FIGS. 9A and 9B, the retractor assembly of FIG. 12, and a driver.
Figure 13B:
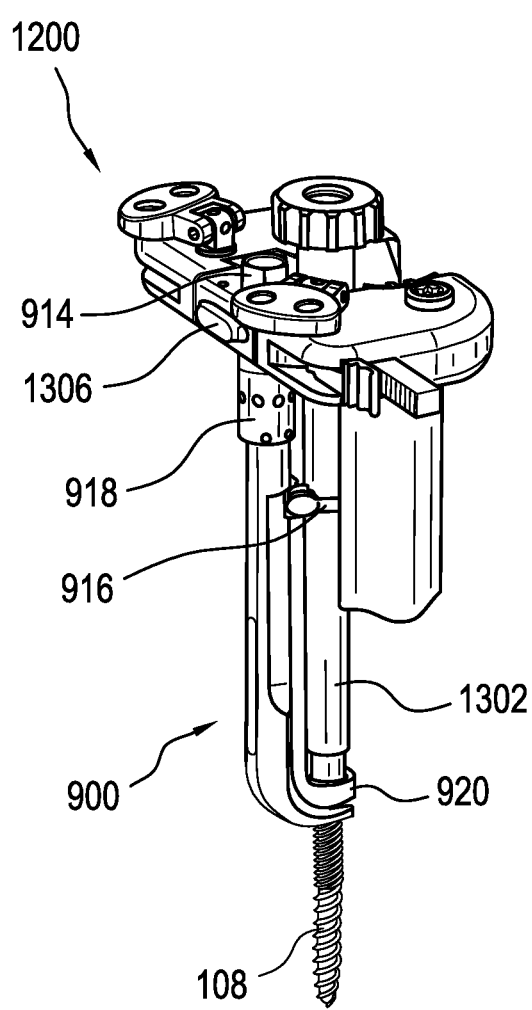
FIG. 13B is a rear perspective view of the assembly of FIG. 13A.

FIGS. 13A and 13B illustrate the retractor assembly 1200 coupled to the support instrument 900 and the anchor 108. Moreover, a driver 1302 is inserted through the driver guide 916 and the lumen defined by the ring-shaped projection 920 of the lock body 904 to interface with the drive feature 502 of the anchor 108. The driver 1302 can include a proximal end 1304 configured to be rotated by hand or using a tool to aid in implanting or adjusting a position of the anchor 108.

Figure 14:
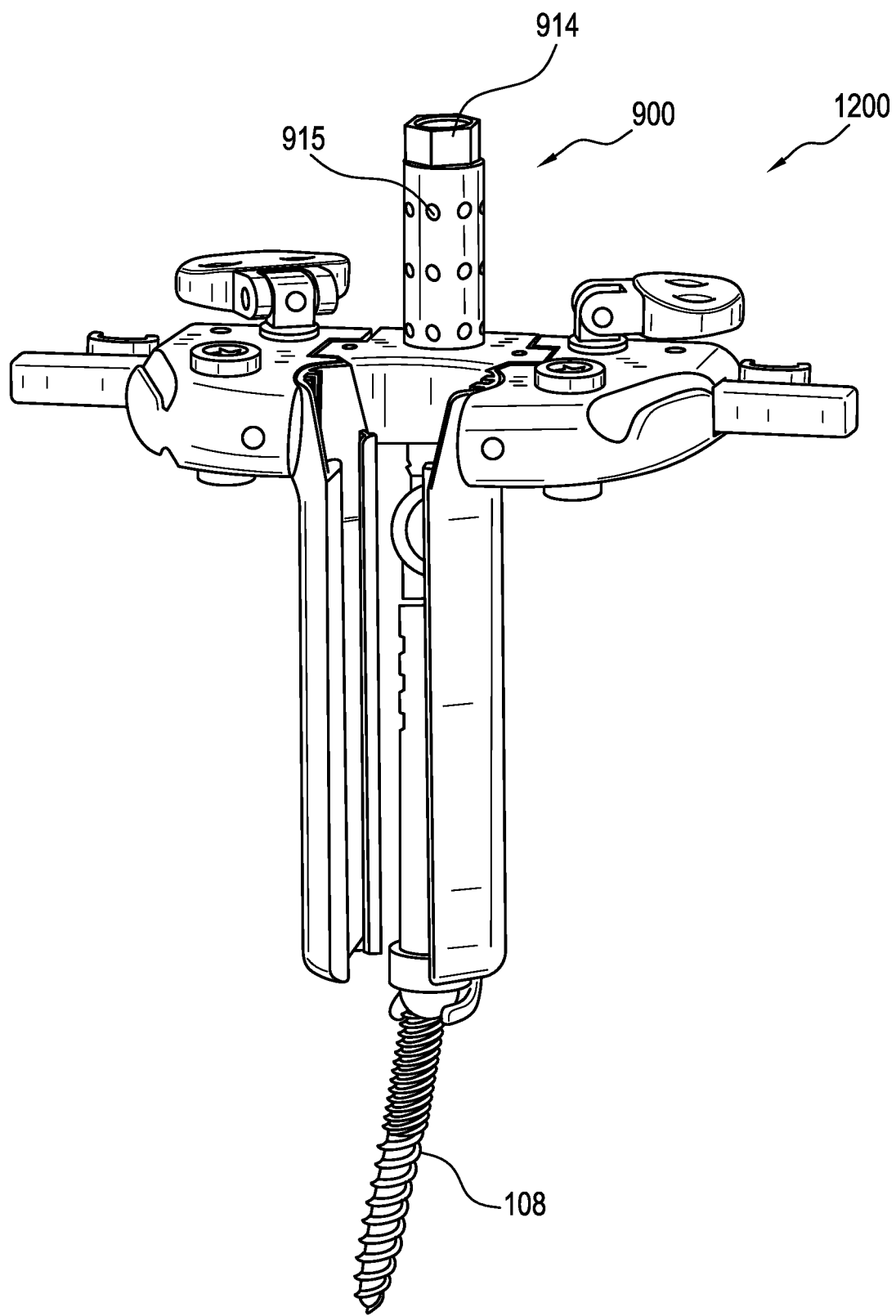
FIG. 14 is a front perspective view of one embodiment of a surgical instrument assembly including the extension of FIGS. 9A and 9B, as well as the retractor assembly of FIG. 12.

FIG. 13B also illustrates a lock release 1306 that can, for example, retract one or more locking pins inserted into the one or more holes 915 formed in the proximal portion 918 of the support instrument 900. Similarly, when a user first couples the instrument 900 and retractor 1200, the lock release 1306 can be depressed to allow the retractor to slide along a length of the elongate body proximal portion 918 without interference. At a desired position along the elongate body, the lock release 1306 can be released, thereby advancing the one or more locking pins into one or more holes formed in the elongate body to lock the relative position and/or orientation of the retractor and the elongate body. Any of a variety of positions along a length of the elongate body can be selected. For example, in the embodiment shown in FIGS. 13A and 13B, only the distal end 914 of the instrument 900 can be seen above an upper surface of the retractor assembly 1200. In FIG. 14, in contrast, the retractor 1200 is shown at a more distal position along a length of the instrument 900 or elongate body 902 thereof. In addition to the distal end 914, several levels of holes 915 are visible above an upper surface of the retractor 1200.

Figure 15:
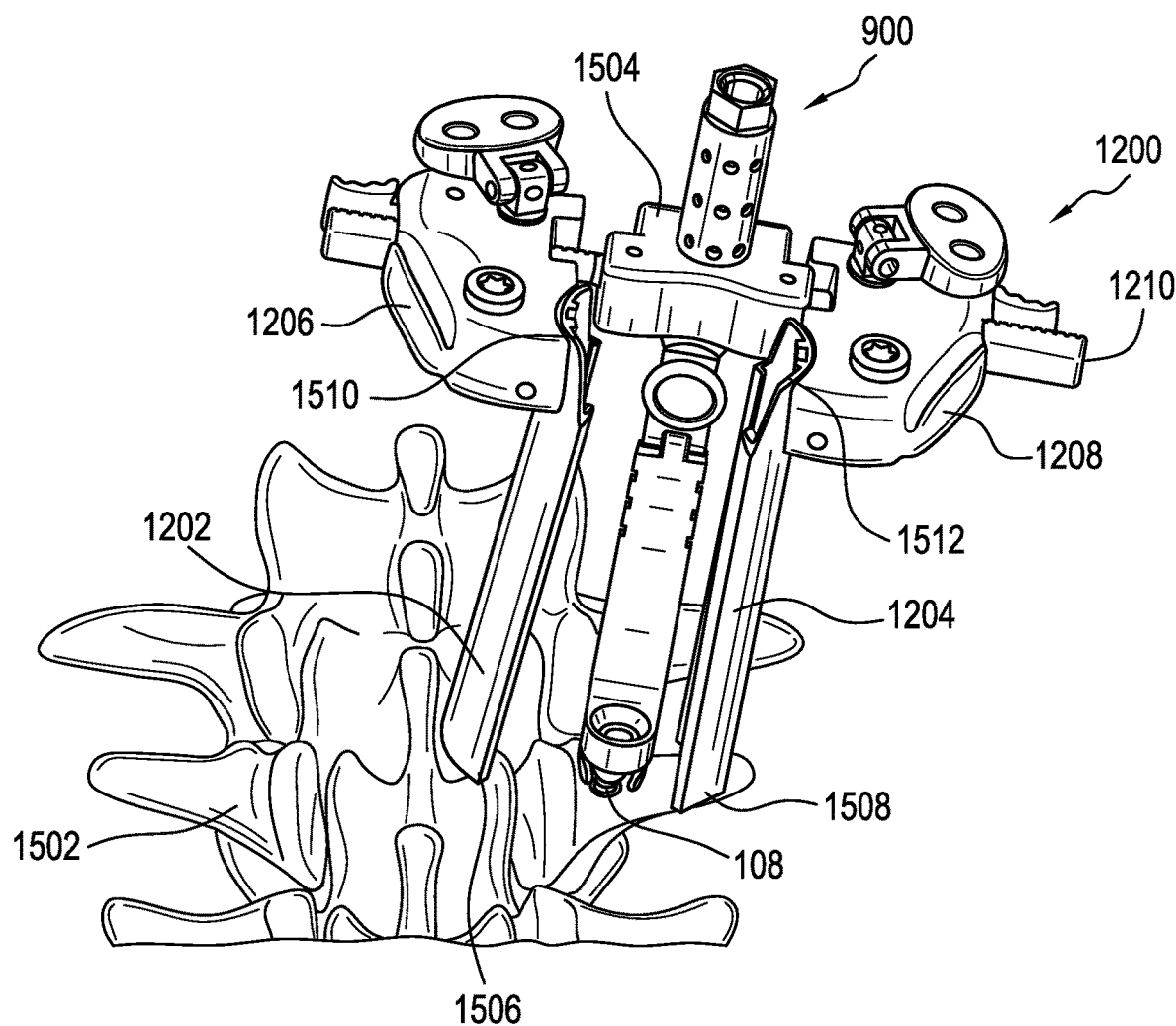
FIG. 15 is a front perspective view of the surgical instrument assembly of FIG. 14 implanted in a patient's spine.
Figure 16:
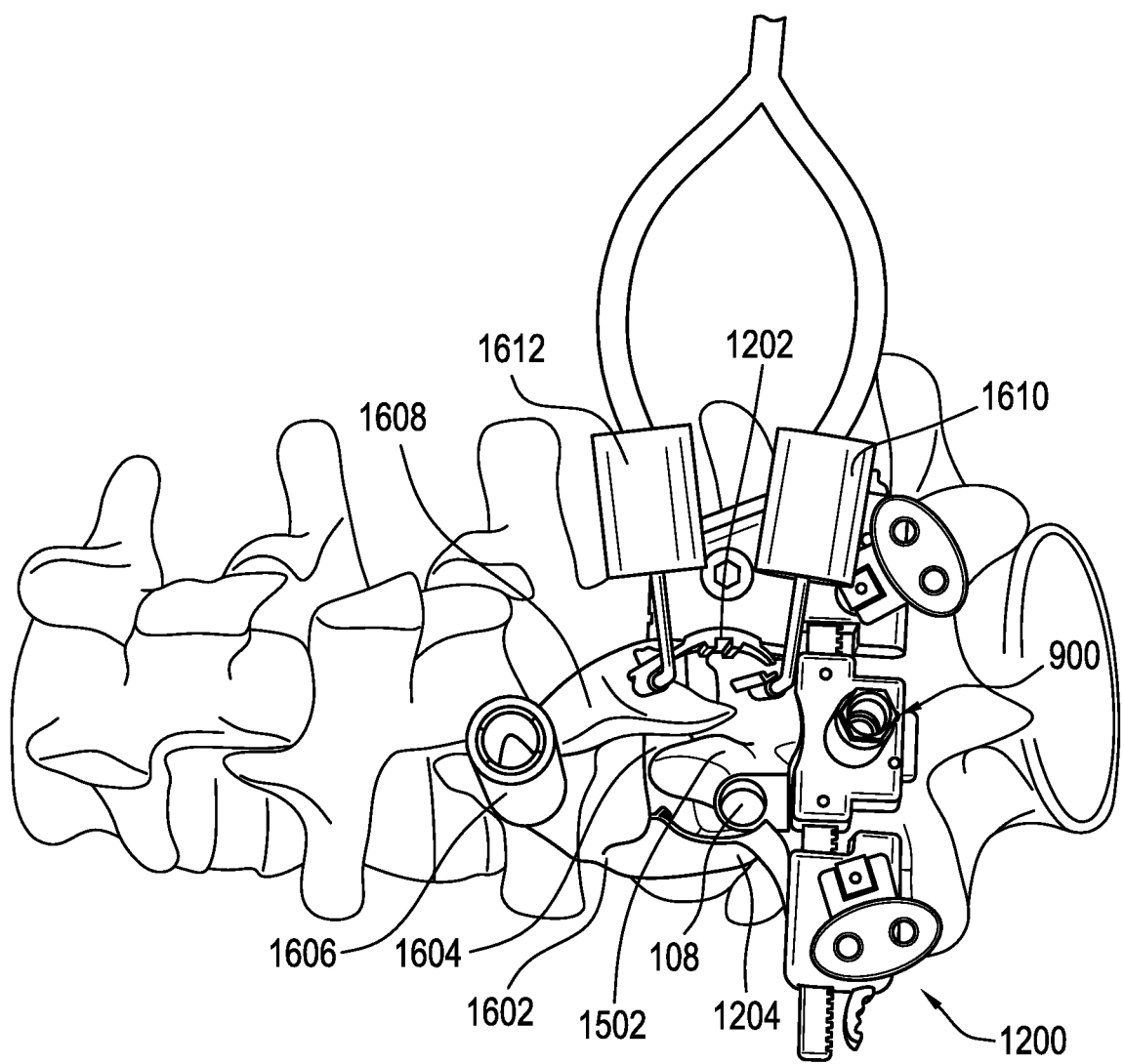
FIG. 16 is a top view of the assembly of FIG. 14 implanted in a patient's spine with other instruments performing medial-lateral tissue retraction.

FIGS. 15 and 16 illustrate the retractor assembly 1200 coupled to the support instrument 900 and the anchor 108 implanted in a patient's vertebra 1502. As mentioned above, a surgical procedure according to the teachings provided herein can include forming an incision 1602 in a patient's skin and tissue above the implantation site. The anchor 108 can then be implanted in the patient's vertebra 1502. The anchor can be implanted alone and the support instrument 900 and retractor assembly 1200 can be coupled thereto after implantation either together or sequentially. Alternatively, the entire assembly of the anchor 108, instrument 900, and retractor 1200 can be implanted together using a driver, as shown in FIGS. 13A and 13B.

Once coupled to the anchor, the instrument 900 and retractor 1200 can be positioned relative to the anchor 108 as shown. This can be done, for example, by manually manipulating the instrument 900 and retractor 1200 to move them polyaxially relative to the anchor 108. When a desired position is reached, for example, as shown in FIGS. 15 and 16 wherein the opposed tissue manipulating implements 1202, 1204 are configured to retract tissue in the medial and lateral directions relative to the patient, the position of the instrument 900 can be locked using the actuator 906.

A position of the retractor 1200 along the instrument 900 can be adjusted if necessary to achieve a desired height of the tissue manipulating implements 1202, 1204. Alternatively, if so equipped a length of each tissue manipulating implement can be adjusted to a desired height. For example, the tissue manipulating implements can be adjusted such that they extend into the incision 1602 and abut against the tissue on the medial and lateral sides of the incision.

To enable better access to, for example, an intervertebral disc 1604 adjacent to the vertebra 1502, the tissue manipulating implements 1202, 1204 can be any of translated away from one another and toed away from one another in the medial and lateral directions relative to the patient. FIG. 15 illustrates one possible combination of such movements, wherein the tissue manipulating implements 1202, 1204 have both been translated medially and laterally away from one another along the rack 1210 (e.g., see separation of the housings 1206, 1208 from the central portion 1504 of the rack). Moreover, the tissue manipulating implement 1202 is shown toed away from the implement 1204, as its distal end 1506 is angled away from the distal end 1508 of the implement 1204. A distance between the proximal ends 1510, 1512 of the implements 1202, 1204 remains unchanged.

FIG. 16 illustrates the tissue retraction that can be provided by moving the tissue manipulating implements in the above-described manner. Namely, the incision 1602 formed in the patient's skin and underlying tissue can be retracted medially and laterally to provide a wider opening and working channel between the tissue manipulating implements to access the patient's spine or intervertebral space. In some embodiments, the working channel can extend to an adjacent implantable anchor 1606 implanted in an adjacent vertebra 1608. The adjacent implanted anchor 1606 can be any of a number of anchor and/or extension assemblies known in the art. Examples of such assemblies are described in U.S. Pat. No. 7,179,261 entitled "PERCUTANEOUS ACCESS DEVICES AND BONE ANCHOR ASSEMBLIES," the entire contents of which is incorporated by reference herein.

FIG. 16 also illustrates that other surgical instruments can be introduced into the working channel defined by the tissue manipulating implements 1202, 1204 and, in some embodiments, one or more instruments can be coupled to one or more of the tissue manipulating implements. For example, a light or illumination source 1610 can be coupled to one of the tissue manipulating implements to illuminate the working channel. Alternatively or in addition, a visualization system 1612, such as a camera, can be coupled to one of the implements 1202, 1204 to provide magnified viewing of the working channel on an external monitor, etc.

Once the tissue of the incision walls is retracted to form the working channel, any of a variety of surgical procedures can be performed by introducing one or more instruments through the working channel defined by the tissue manipulating implements of the retractor assembly. For example, procedures on the intervertebral disc space, such as disc replacement, discectomy, endplate preparation, fusion cage insertion, bone graft delivery, and the like can be performed by passing instruments or implants through the working channel.

Figure 17A:
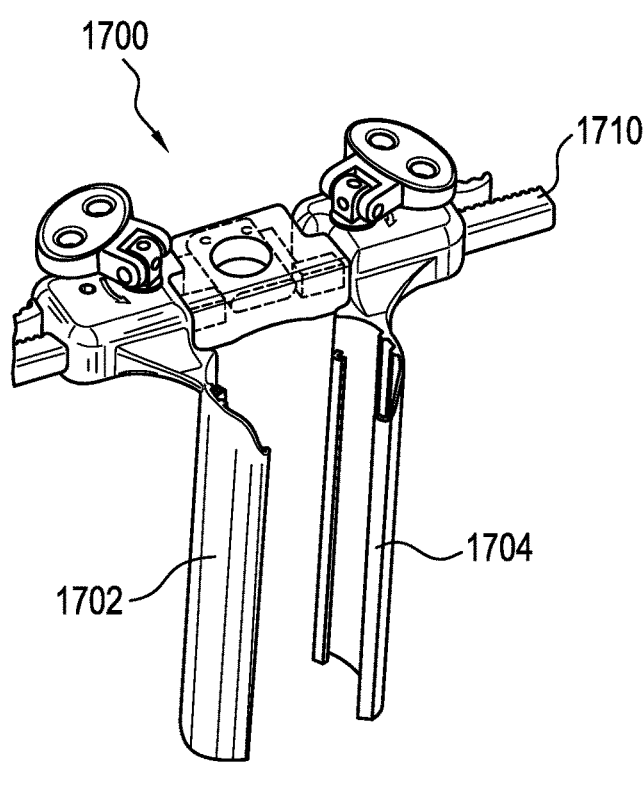
FIG. 17A is a front perspective view of another embodiment of a retractor assembly according to the teachings provided herein.
Figure 17B:
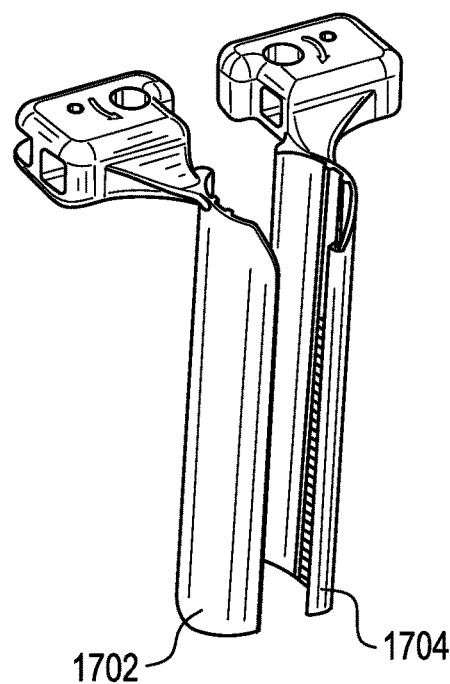
FIG. 17B is a front perspective view of tissue manipulating implements of the retractor assembly of FIG. 17A.
Figure 18A:
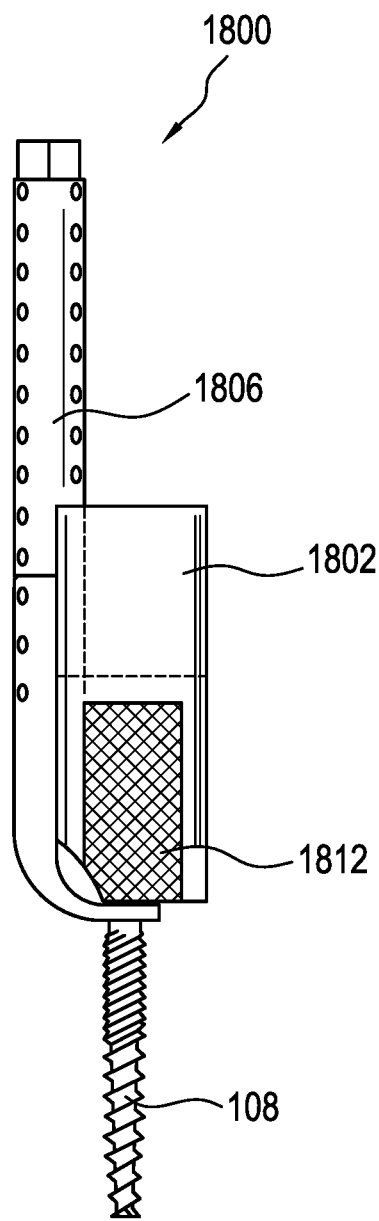
FIG. 18A is a side view of one embodiment of a surgical instrument including tissue manipulating implements coupled thereto.
Figure 18B:
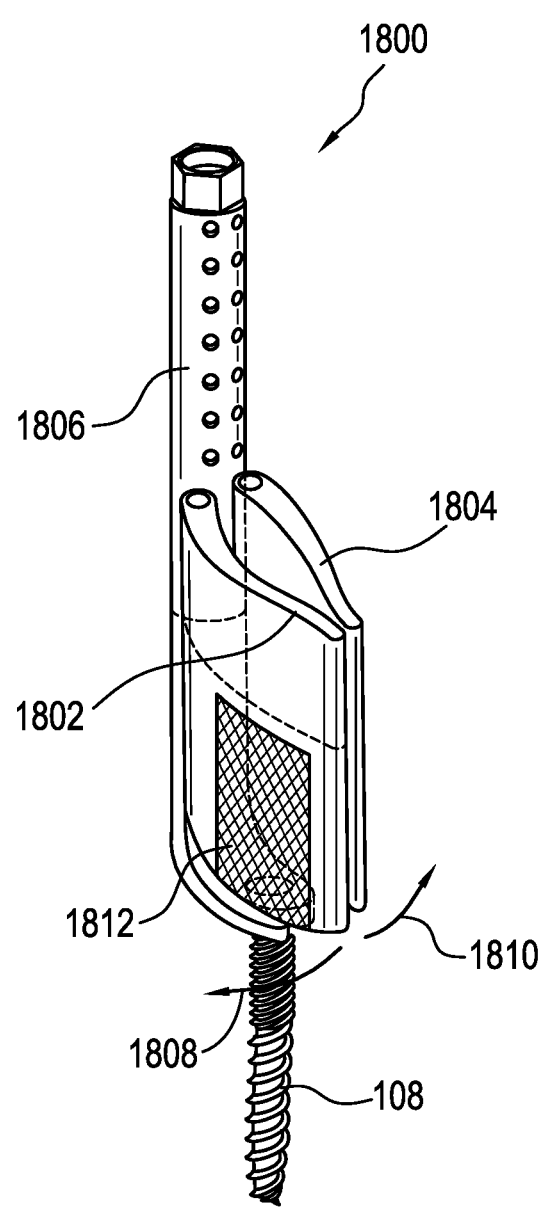
FIG. 18B is a front perspective view of the instrument of FIG. 18A.
Figure 18C:
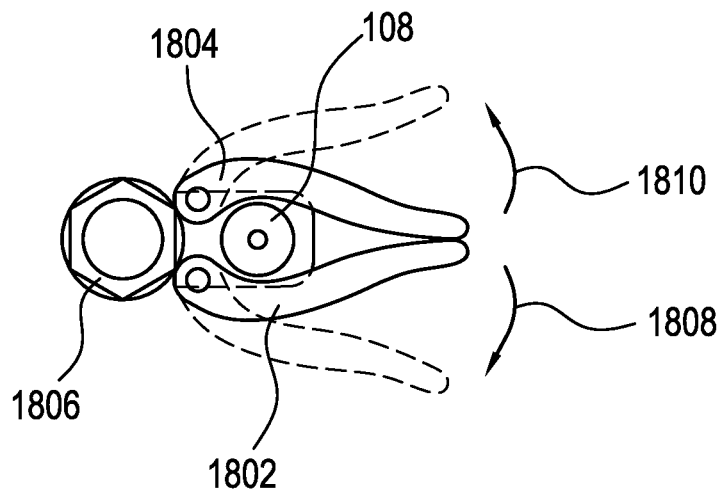
FIG. 18C is a top view of the instrument of FIG. 18A.

A number of variations and alternative embodiments to the instruments and assemblies described above are also possible. In FIGS. 17A and 17B, for example, a retractor 1700 is shown that only provides for translation of its tissue manipulating implements 1702, 1704 toward or away from one another along its rack 1710. The implements 1702, 1704, as shown in FIG. 17B, do not include any mechanism for toeing relative to one another. In some embodiments, however, this can allow the implements to be smaller and lower profile than those described above.

FIGS. 18A-25 illustrate still other embodiments in which tissue manipulating implements are more directly incorporated into a support instrument that couples to an anchor and provides selective polyaxial movement relative thereto. Such embodiments can eliminate the need for a separate retractor assembly. In the embodiment shown in FIGS. 18A-19 for example, opposed tissue manipulating implements or blades 1802, 1804 can be pivotably coupled to the elongate body 1806 of the instrument 1800. Accordingly, the instrument 1800 can be introduced into an incision in the configuration of FIG. 18B wherein the tissue manipulating implements are in contact with one another and can easily pass into the incision. The implements can then be pivoted away from one another in the direction of arrows 1808, 1810 to retract the tissue forming the incision walls and provide a larger working channel for a surgeon, as shown in FIG. 18C.

Figure 19:
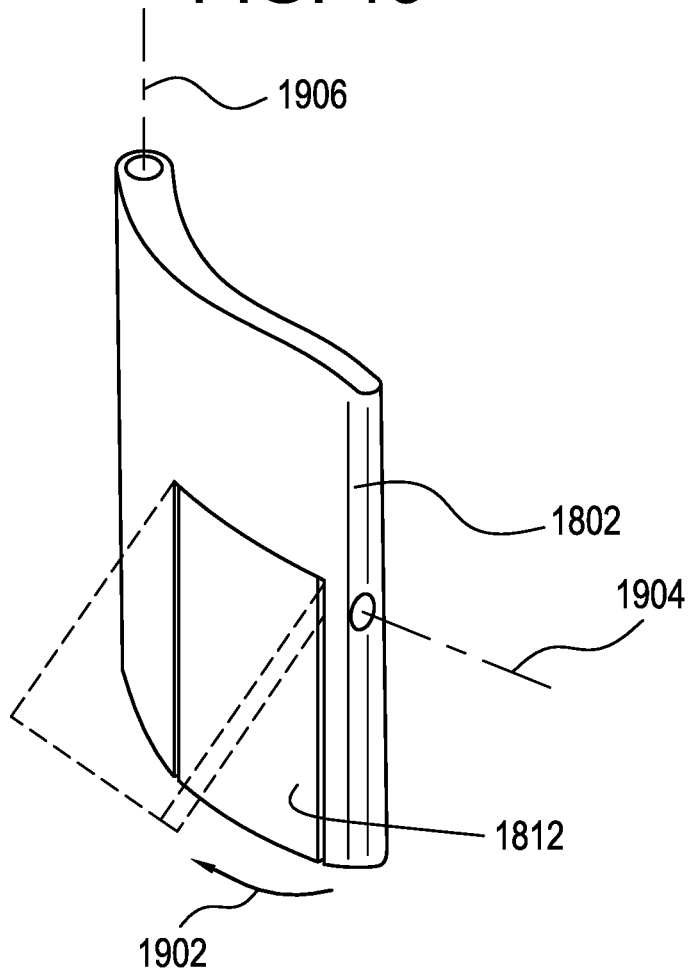
FIG. 19 is a front perspective view of one of the tissue manipulating implements of the instrument of FIG. 18A.
Figure 20:
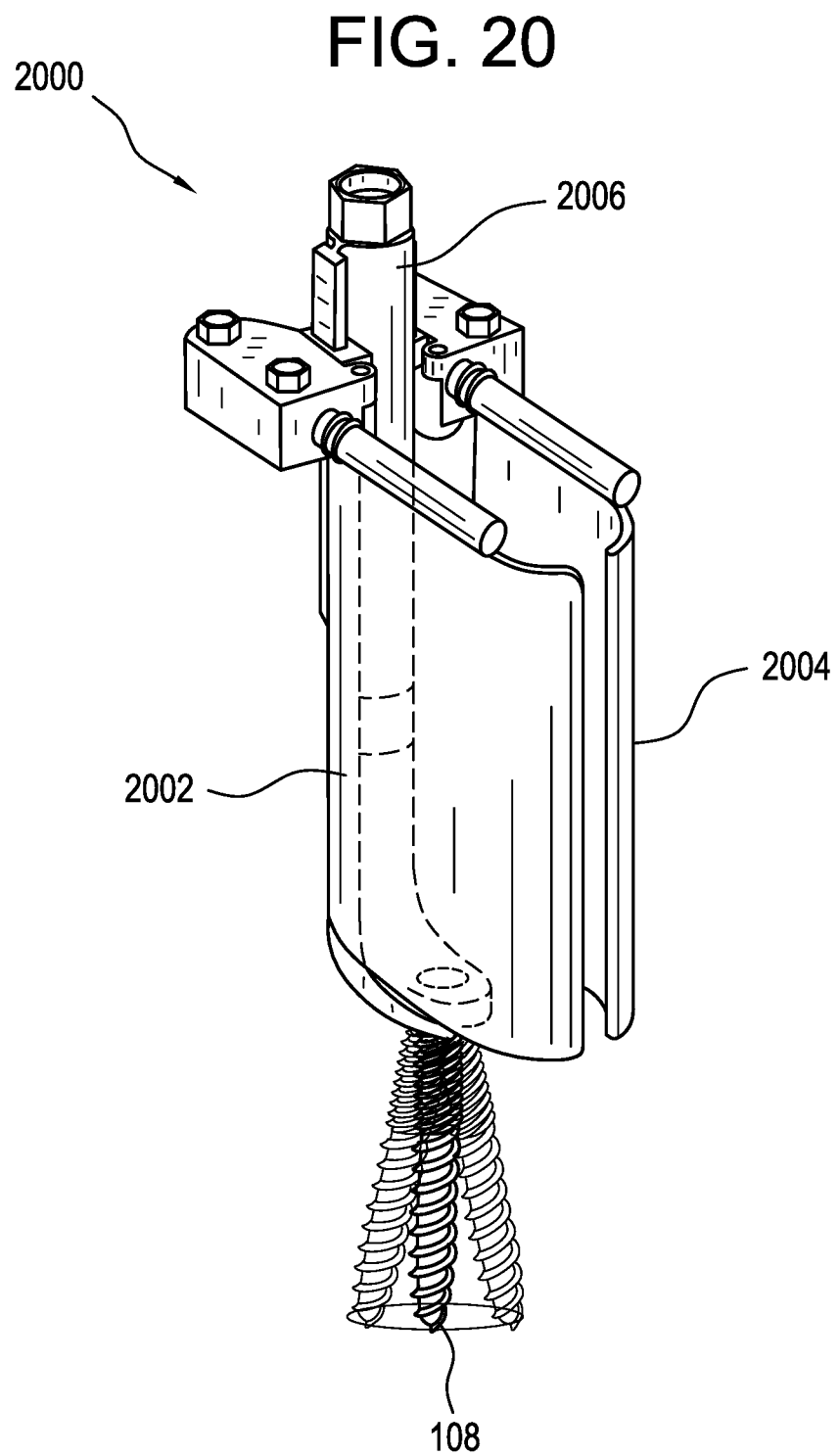
FIG. 20 is a front perspective view of another embodiment of a surgical instrument including tissue manipulating implements coupled thereto.

Moreover, each tissue manipulating implement 1802, 1804 can include a distal portion 1812 that can be pivotably coupled to the remainder of the implement. As shown in FIG. 19, the distal portion 1812 can be configured such that a distal end of the implement 1802 or 1804 can pivot away from the remainder of the implement to approximate toeing movement of the implement that can aid in tissue retraction. In some embodiments, the pivot axis 1904 of the distal portion 1812 can be transverse to the pivot axis 1906 of the implement 1802.

FIGS. 20-25 illustrate still another embodiment of an instrument 2000 wherein individual tissue manipulating implements 2002, 2004 can be selectively coupled to opposed sides of the elongate body 2006 of the instrument. As shown in FIG. 21, for example, the instrument 2000 can include an elongate body 2006 configured to couple to the anchor 108 and provide selective polyaxial movement relative thereto. The elongate body 2006 can include mating features 2008 formed on opposed sides thereof. The mating features can be, for example, a slot or protrusion formed along a length of the elongate body.

Figure 23:
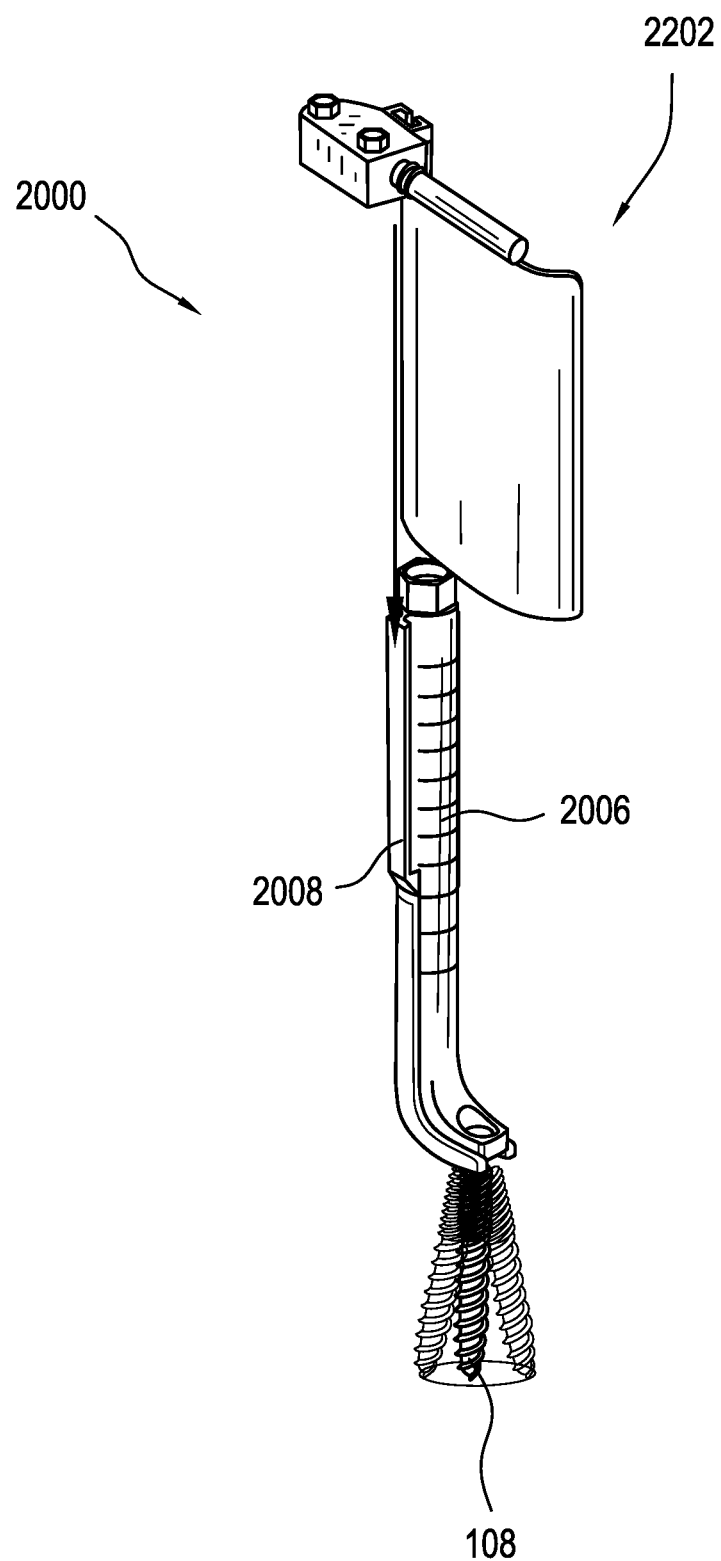
FIG. 23 is a front perspective view of coupling an anchor extension and a tissue manipulating implement of the instrument of FIG. 20.

A tissue manipulating implement 2002 can be coupled to the elongate body 2006 by sliding a complementary mating feature of the implement over the mating feature 2008 on the elongate body, as shown in FIG. 23. Any of a variety of mechanisms, such as the pawl or locking pins described above, can be utilized to set a height of the implement along the elongate body 2006. Moreover, and as shown in FIG. 22, a blade 2202 can be modular with respect to a base 2204 of the tissue manipulating implement 2002, so in some embodiments the height of the implement 2002 relative to the elongate body 2006 need not be adjustable, as a blade 2202 of a desired height can be selected. In some embodiments, however, both adjustment mechanisms can be included.

Figure 24A:
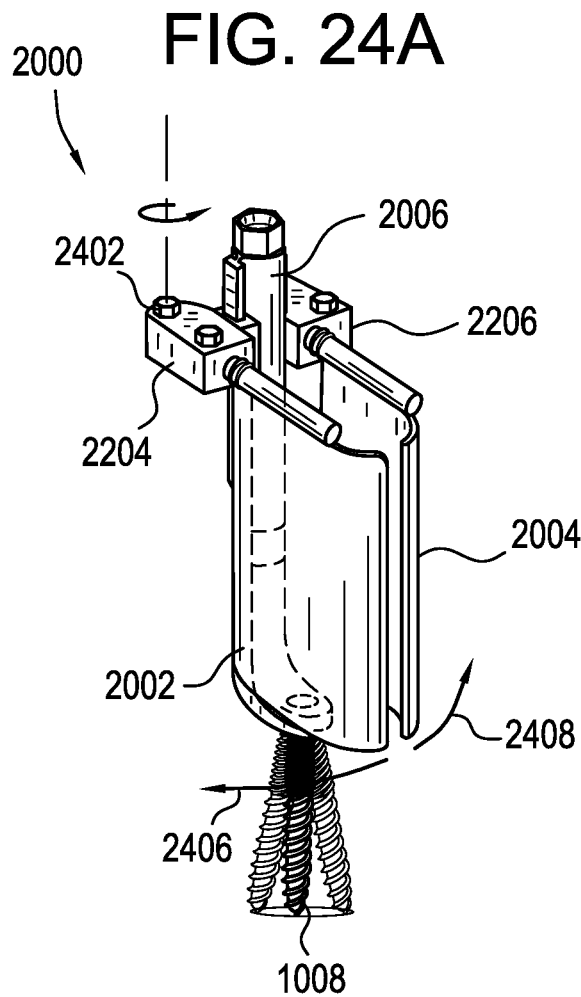
FIG. 24A is an alternative front perspective view of the instrument of FIG. 20 showing a first type of relative movement between tissue manipulating implements.
Figure 24B:
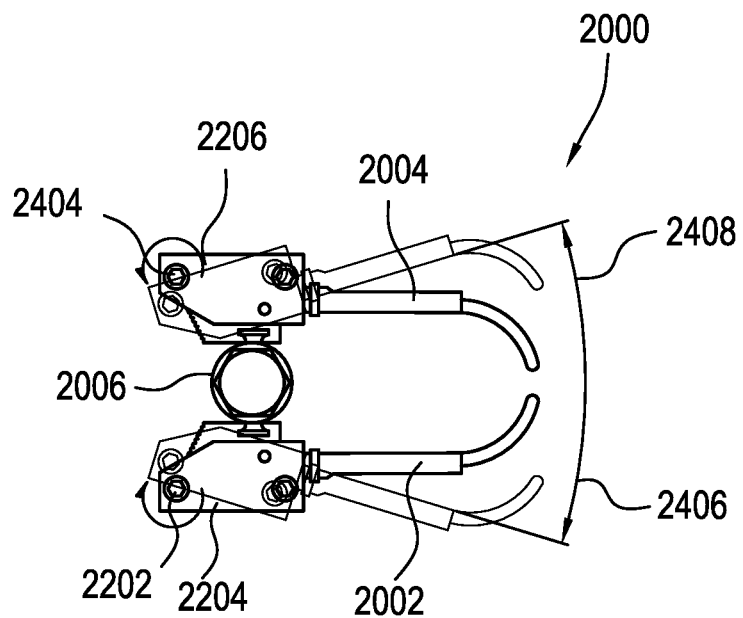
FIG. 24B is an alternative top view of the instrument of FIG. 20 showing a first type of relative movement between tissue manipulating implements.
Figure 25:
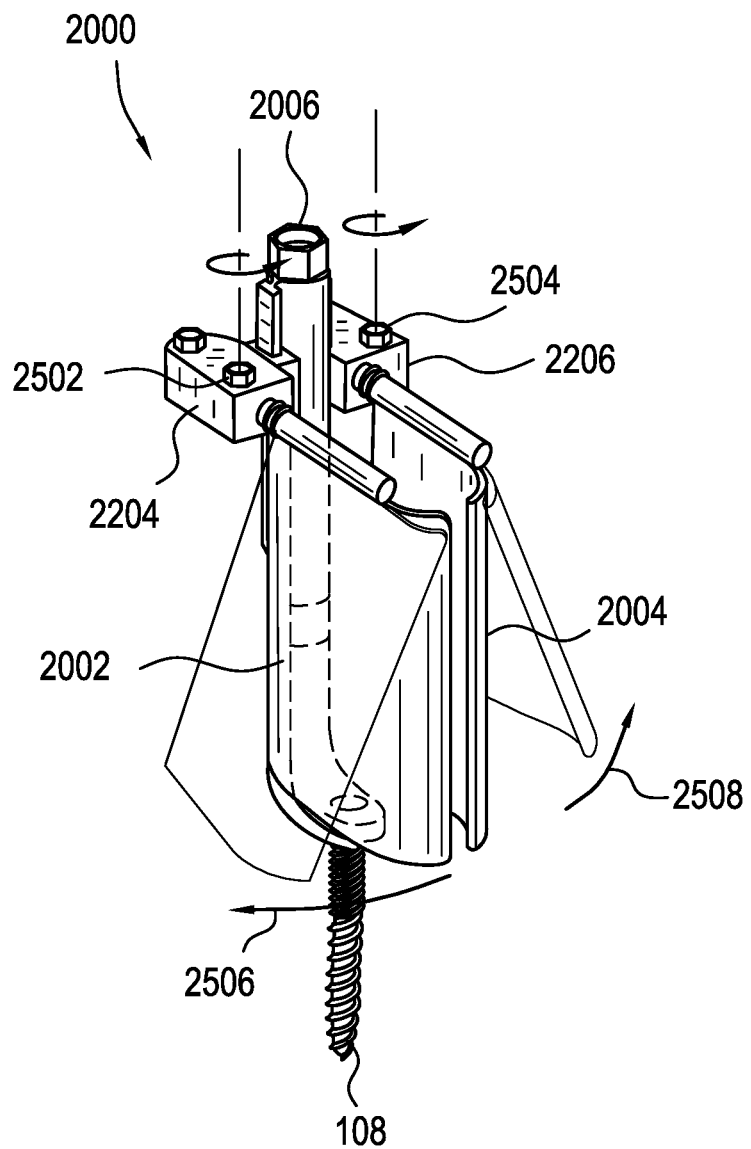
FIG. 25 is an alternative front perspective view of the instrument of FIG. 20 showing a second type of relative movement between tissue manipulating implements.

FIGS. 24A-25 illustrate the various degrees of freedom of the tissue manipulating implements 2002, 2004 once coupled to the elongate body 2006. For example, rotation of a first actuator 2402, 2404 on each base 2204, 2206 can cause the tissue manipulating implements 2002, 2004 to pivot away from one another, as shown by arrows 2406, 2408. The pivot axis of each implement 2002, 2004 can be parallel to a longitudinal axis of the elongate body 2006.

Moreover, rotation of a second actuator 2502, 2504 on each base 2204, 2206 can pivot the implements 2002, 2004 about an axis transverse to the longitudinal axis of the elongate body 2006 to create a toeing movement, as shown by arrows 2506, 2508 of FIG. 25. This toeing movement can involve distal ends of the tissue manipulating implements 2002, 2004 moving away from one another while a distance between proximal ends thereof remains unchanged.

Figure 26:
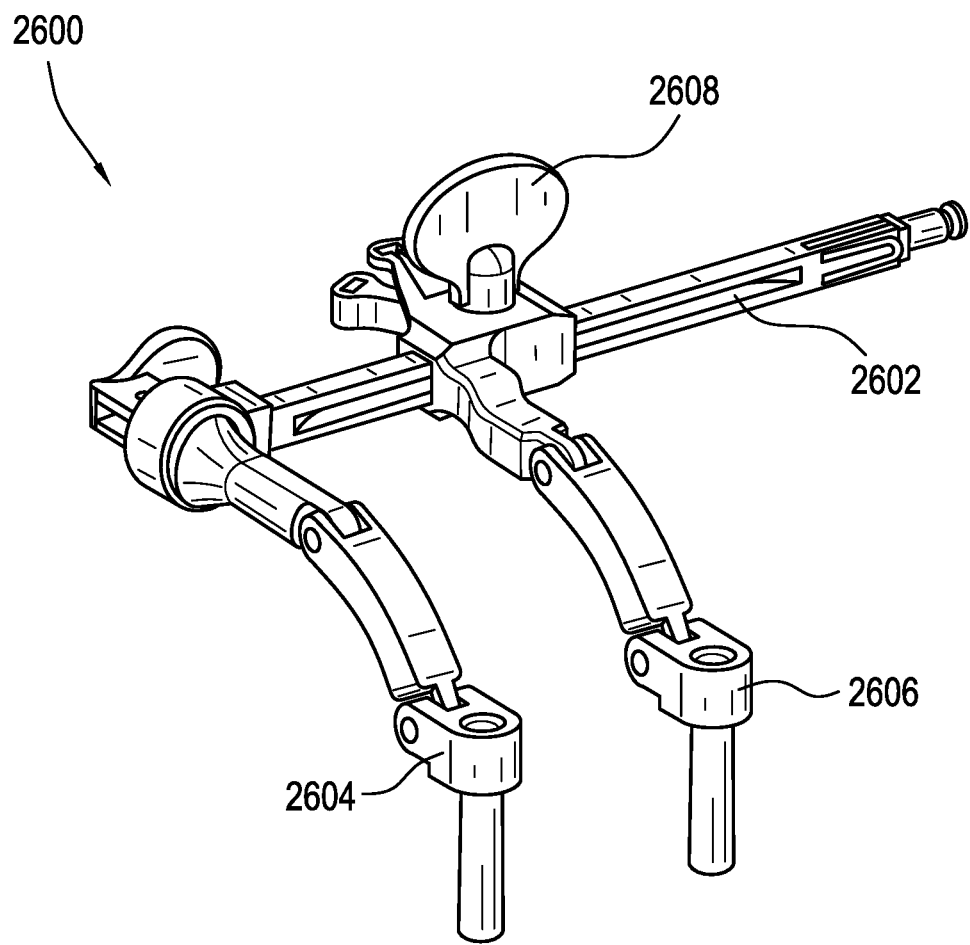
FIG. 26 is a side perspective view of one embodiment of a spinal distraction instrument according to the teachings provided herein.

FIGS. 26-31B illustrate various embodiments of instruments for distracting adjacent vertebrae and their use with the support instruments and retractor assemblies described herein. For example, FIG. 26 illustrates one embodiment of a distractor 2600 that includes a rack 2602 and two interfaces 2604, 2606 for coupling with any of an anchor or an instrument coupled to an anchor. The interface 2604 can be anchored to one end of the rack 2602 and the interface 2606 can be coupled to the rack 2602 via a pawl, cog, gear, or other feature that can interface with a series of teeth, recesses, or other features formed along a length of the rack. A thumbwheel 2608 can be coupled to the cog or gear to control movement of the interface 2606 along the rack 2602.

Figure 27A:
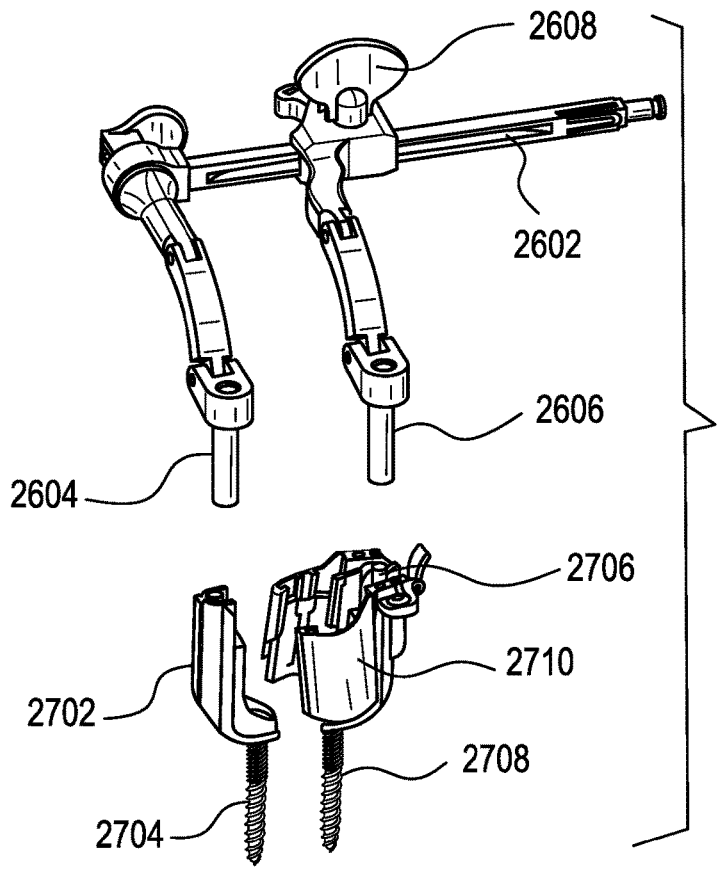
FIG. 27A is a side perspective view of the distraction instrument of FIG. 26 coupling with other surgical instruments described herein.
Figure 27B:
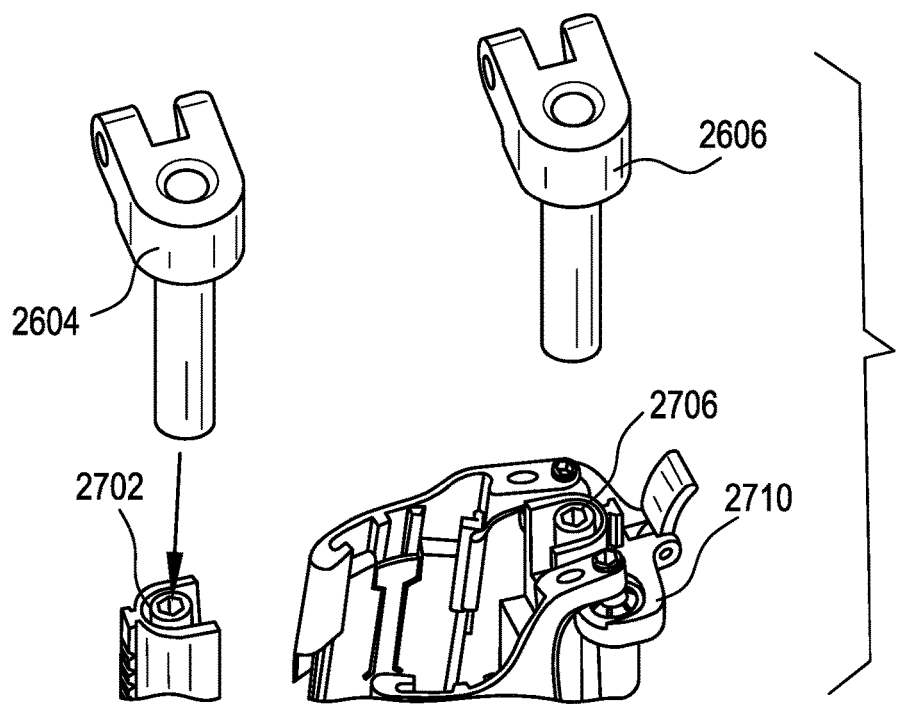
FIG. 27B is a detail view of distal ends of the distraction instrument of FIG. 26 approaching the other surgical instruments shown in FIG. 27A.
Figure 28:
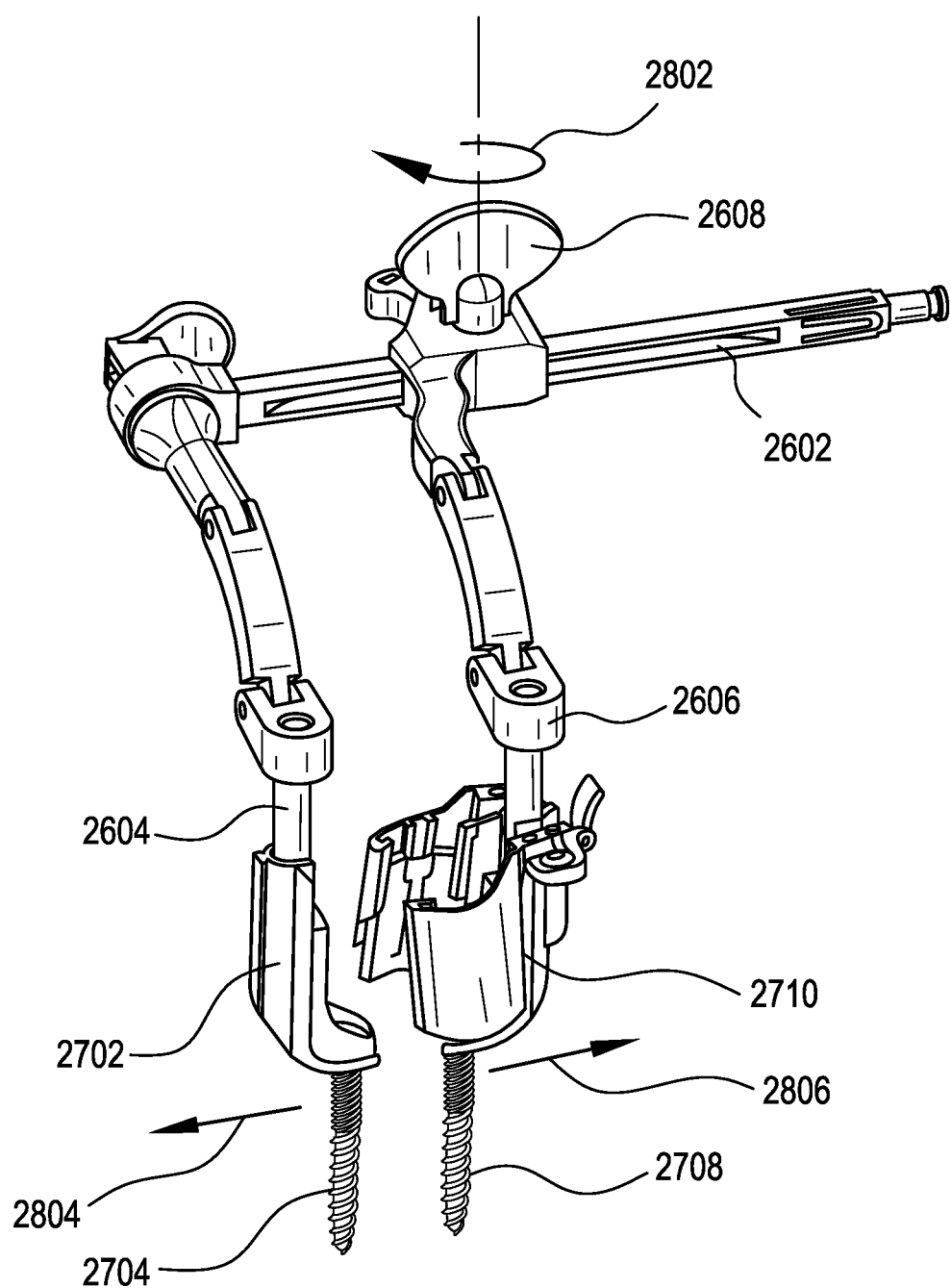
FIG. 28 is a side perspective view of the spinal distraction instrument of FIG. 26 applying a distraction force to the other surgical instruments shown in FIG. 27A.
Figure 29:
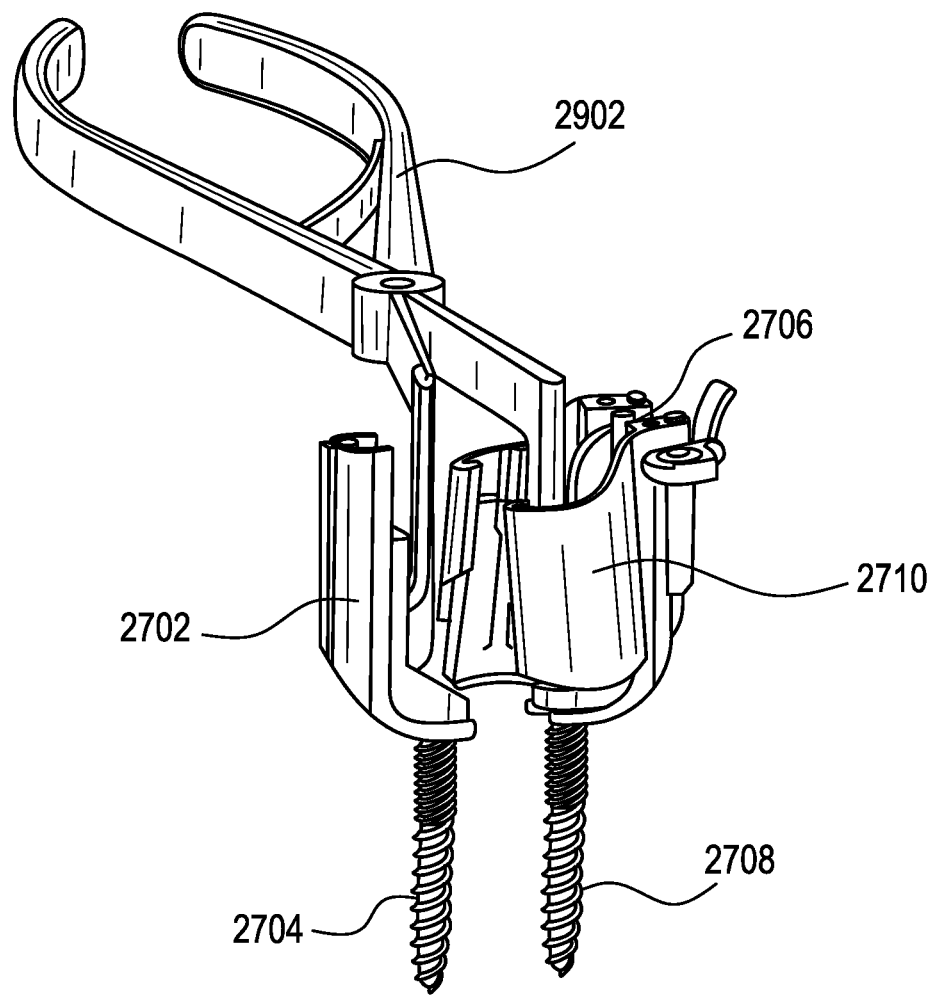
FIG. 29 is a side perspective view of another embodiment of a spinal distraction instrument according to the teachings provided herein.
Figure 30:
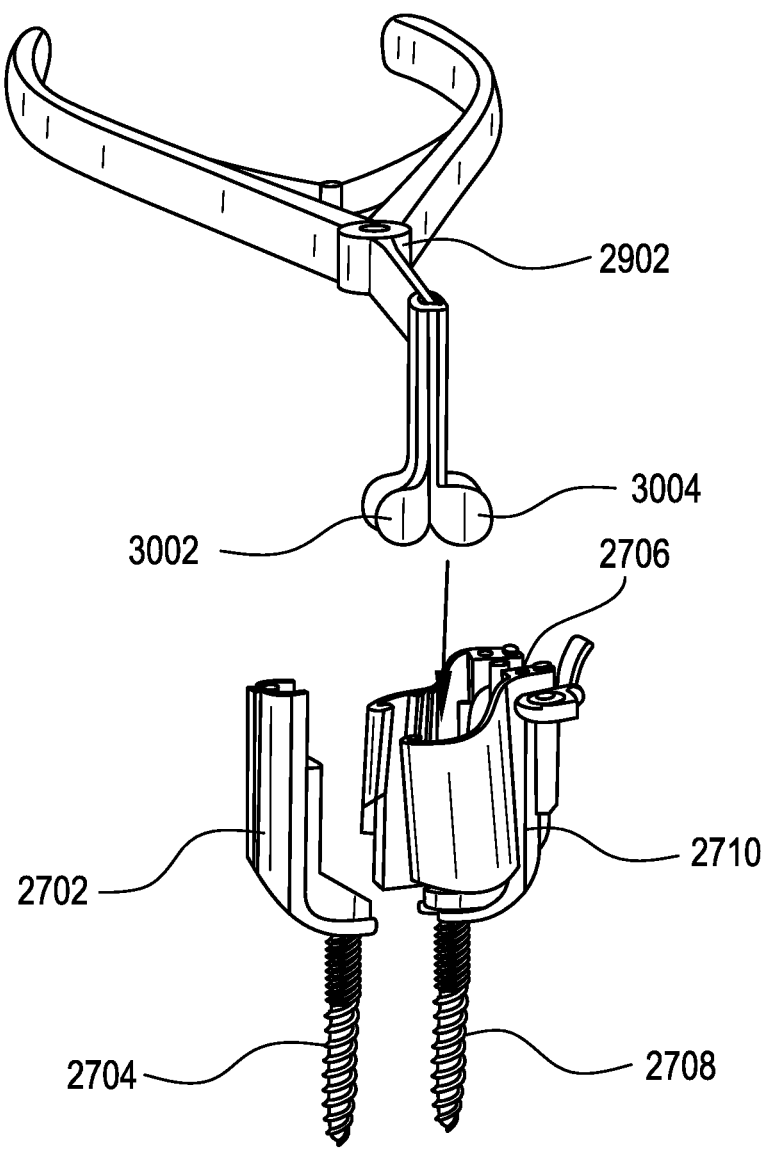
FIG. 30 is a side perspective view of the distraction instrument of FIG. 29 coupling with other surgical instruments described herein.
Figure 31A:
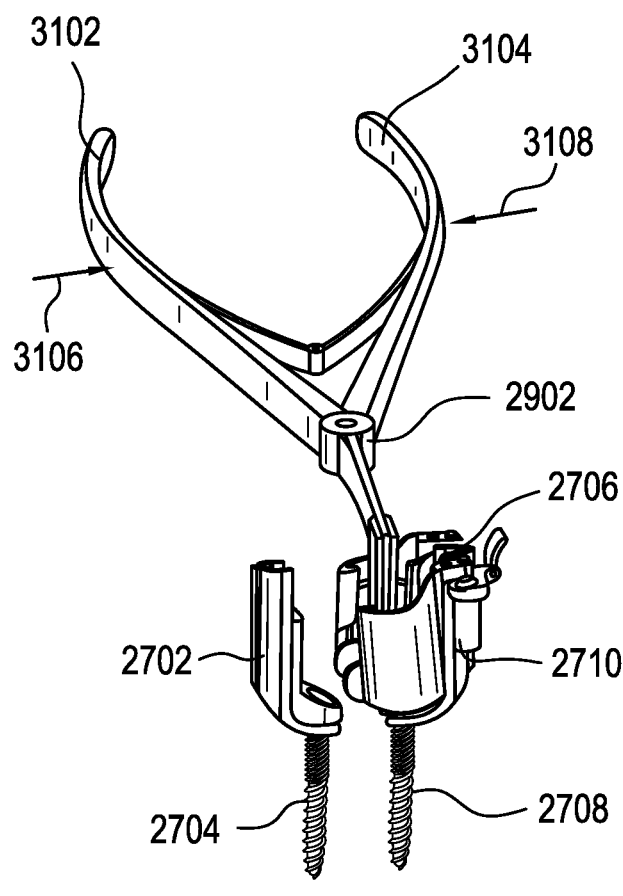
FIG. 31A is a side perspective view of the distraction instrument of FIG. 29 being actuated.
Figure 31B:
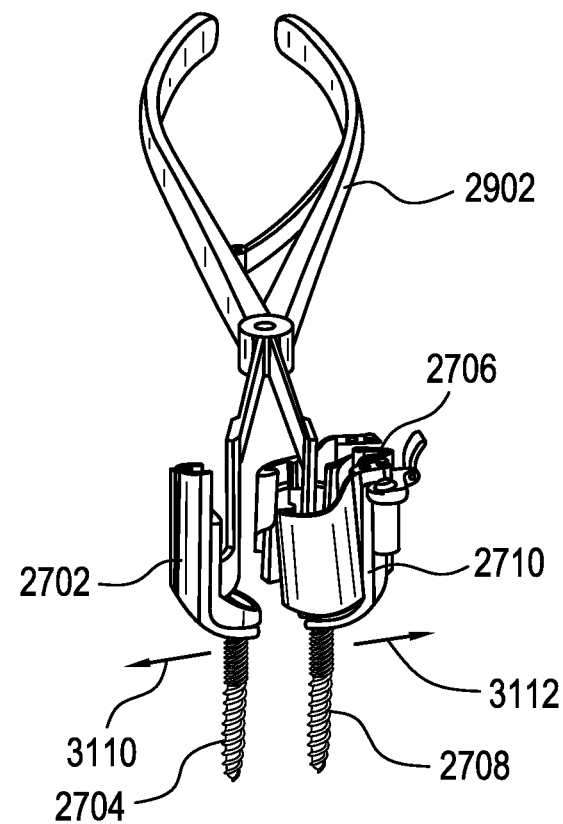
FIG. 31B is a side perspective view of the distraction instrument of FIG. 29 applying a distraction force to the other surgical instruments of FIG. 30.

As shown in FIGS. 27A-28, the interfaces 2604, 2606 can be coupled to anchors implanted in adjacent vertebrae and the thumbwheel 2608 can be rotated to distract the vertebrae by moving the interfaces away from one another along the rack 2602. In the illustrated embodiment, the interfaces can couple to the anchors implanted in the adjacent vertebrae via an extension tower and/or support instrument as described herein that can be coupled to the implanted anchors and locked against movement relative thereto. Accordingly, as shown in FIGS. 27B and 28, the interface 2604 can couple to a proximal end of an extension tower 2702 that is coupled to an anchor 2704 implanted in a first vertebra and the interface 2606 can couple to a proximal end of a support instrument 2706 that is coupled to a second anchor 2708 implanted in a second vertebra. As shown in FIG. 27B, the interfaces 2604, 2606 can include distal ends configured to couple with features formed on proximal ends of the extension tower 2702 and support instrument 2706, e.g., the opposed planar surfaces 814 of the instrument 800 described above. Also note that a retractor assembly 2710 is coupled to the support instrument 2706 to provide, e.g., medial-lateral tissue retraction during the procedure.

Once the distraction instrument 2600 is coupled to the anchors 2704, 2708 implanted in adjacent vertebrae via the extension tower 2702 and support instrument 2706, and the tower and support instrument are locked against movement relative to the anchors, the thumbwheel 2608 or other distraction actuator can be rotated as shown by arrow 2802 in FIG. 28. This can cause the interface 2606 to move away from interface 2604 along the rack 2602, thereby causing corresponding distraction of the anchors 2704, 2708 and the adjacent vertebrae they are implanted into, as shown by arrows 2804, 2806.

In an alternative embodiment illustrated in FIGS. 29-31B, a forceps-like distractor 2902 can be utilized instead of the distractor 2600 described above. Furthermore, the distractor 2902 can include interfaces 3002, 3004 that can be configured to abut against the extension tower 2702 and support instrument 2706 laterally at a position along a length thereof, rather than interfacing with a proximal end thereof, as described above. The method of operation can be similar to that described above, wherein the extension tower 2702 and support instrument 2706 can be locked to prevent movement relative to the implanted anchors 2704, 2708. The interfaces 3002, 3004 can then be inserted into the working channel provided between the opposed tissue manipulating implements of the retractor assembly 2710 and opposed handles 3102, 3104 of the distractor 2902 can be urged toward one another, as shown by the arrows 3106, 3108 of FIG. 31A. This can cause the interfaces 3002, 3004 to move apart from one another, contact the tower 2702 and support instrument 2706, and urge the two components away from one another, as shown by arrows 3110, 3112 of FIG. 31B. Given the rigid implantation of the anchors 2704, 2708 in adjacent vertebrae (not shown), the vertebrae can be drawn away from one another in the same manner.

Figure 32:
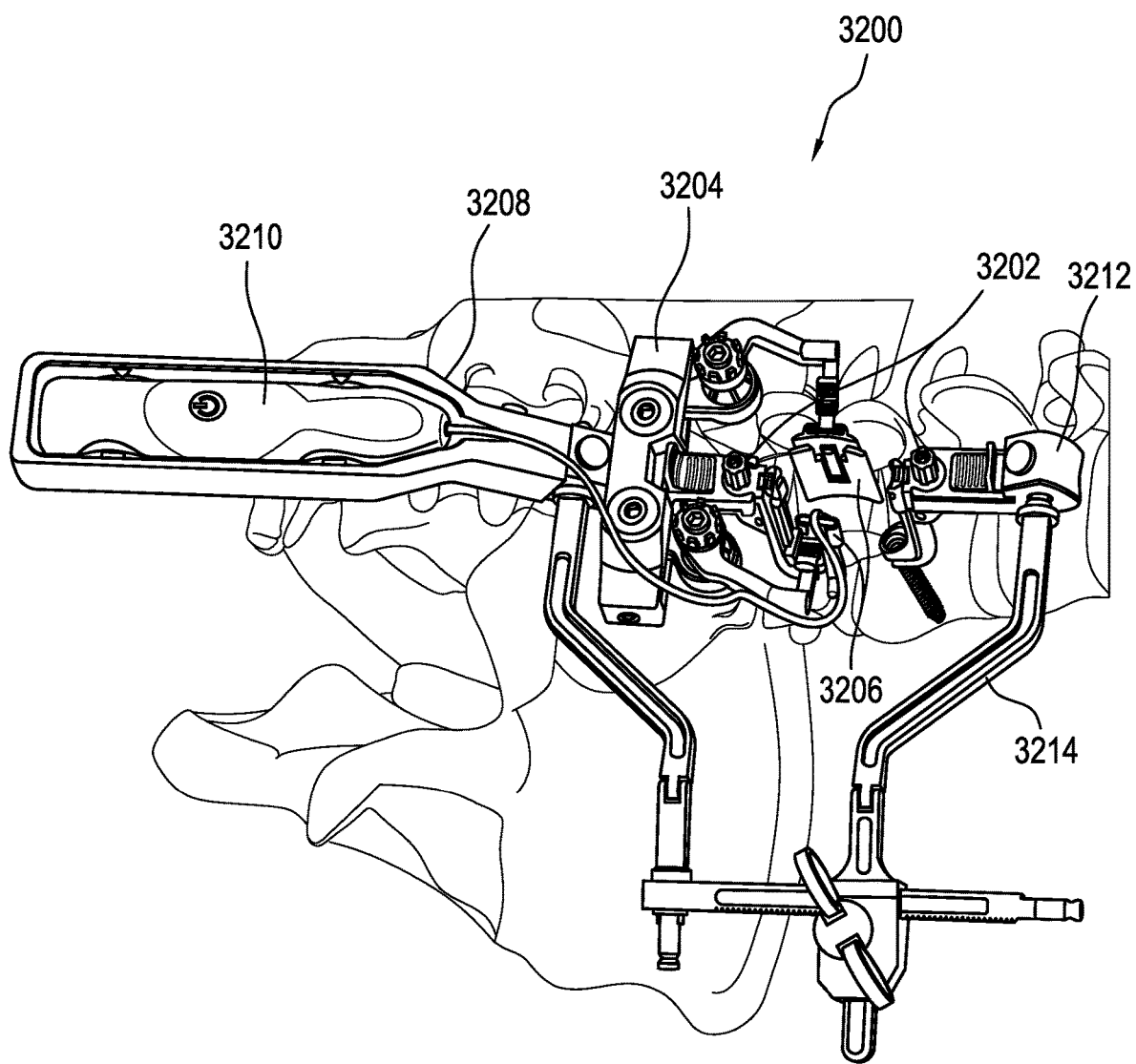
FIG. 32 is a perspective view of one embodiment of a surgical instrument assembly.
Figure 33:
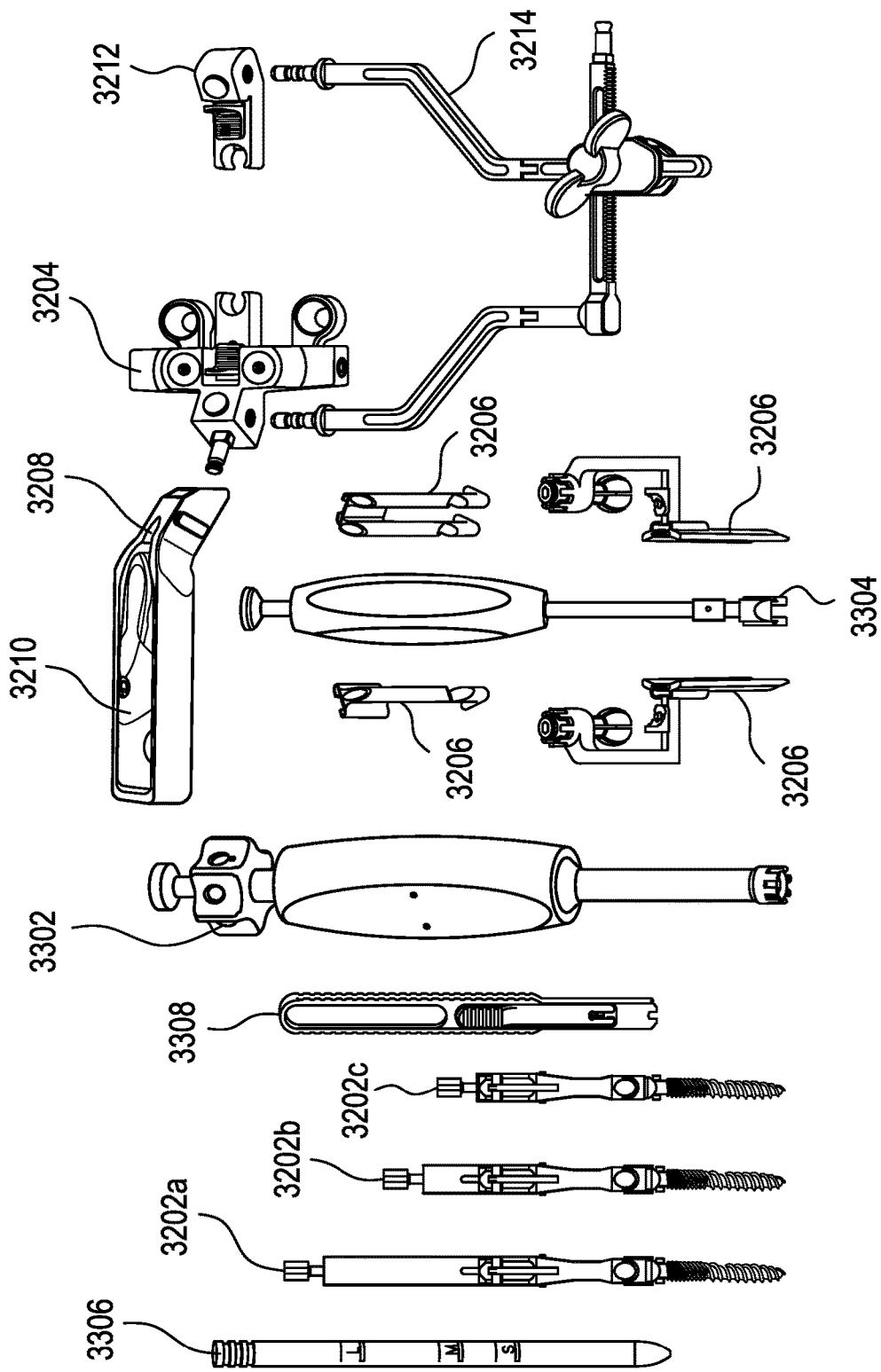
FIG. 33 is an exploded view of the components of the surgical instrument assembly of FIG. 32.

FIGS. 32 and 33 illustrate one embodiment of a surgical retractor system 3200 according to the teachings provided herein. The system can be used to facilitate retraction of skin, muscle, and other soft tissue to access, for example, various portions of a patient's spine. Further, the system can include a retractor and other components docked via surgical instruments as described herein to a patient's body via, e.g., vertebrae, and as a result can be utilized to perform various procedures, including vertebral distraction, etc.

As shown by the assembled system of FIG. 32 and the disassembled view of FIG. 33, the system 3200 can include one or more surgical support instruments 3202 coupled to screws implanted in a patient's vertebrae, a retractor 3204 coupled to a support instrument, one or more tissue manipulating implements 3206 coupled to the retractor, a stability handle 3208 with light source 3210 coupled to the retractor 3204, a distraction module 3212 coupled to another support instrument 3202 from the retractor 3204, and a distraction rack 3214 coupled to the retractor 3204 and the distraction module 3212 to perform distraction, e.g., between adjacent vertebrae. Also shown in FIG. 33 is an actuating instrument 3302 that can be used to couple the tissue manipulating implements 3206 to the retractor 3204 and control positioning/locking thereof, as well as a tissue manipulating implement adjuster 3304 that can be utilized to adjust a position, depth, etc. of an expandable tissue manipulating implement coupled to the retractor 3204. FIG. 33 also illustrates several different sizes of surgical support instruments 3202, e.g., a larger instrument 3202a, a middle-size instrument 3202b, and a smaller instrument 3202c. Finally, FIG. 33 also illustrates a reference stick 3306 that can be utilized to determine the appropriate size of support instrument 3202 and a surgical instrument component removal tool 3308 that can be utilized to separate two part surgical support instruments, as described herein.

Figure 34:
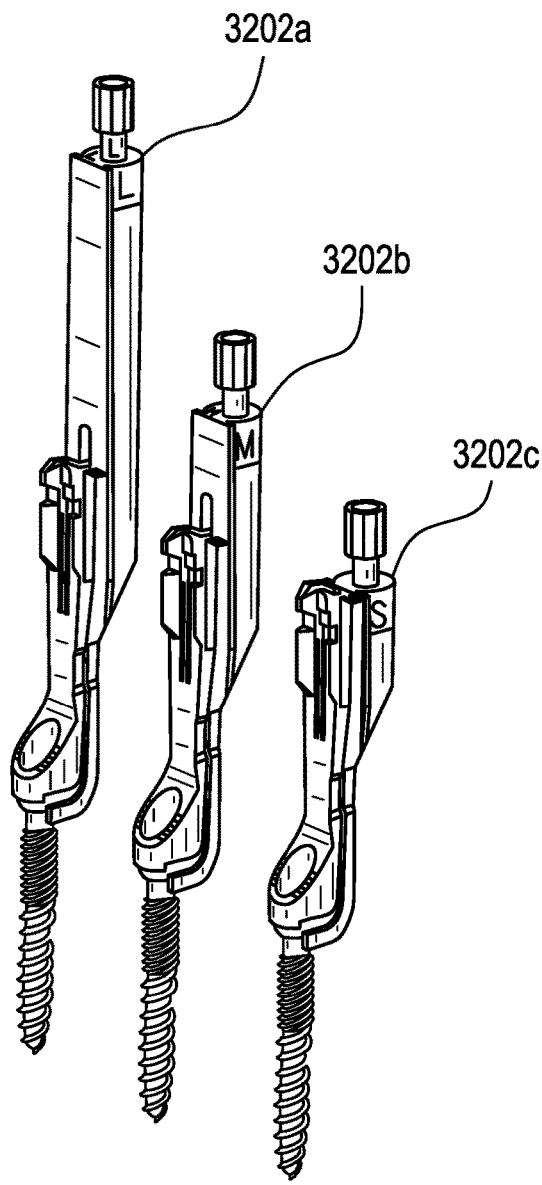
FIG. 34 is a perspective view of various sizes of surgical instruments.
Figure 35A:
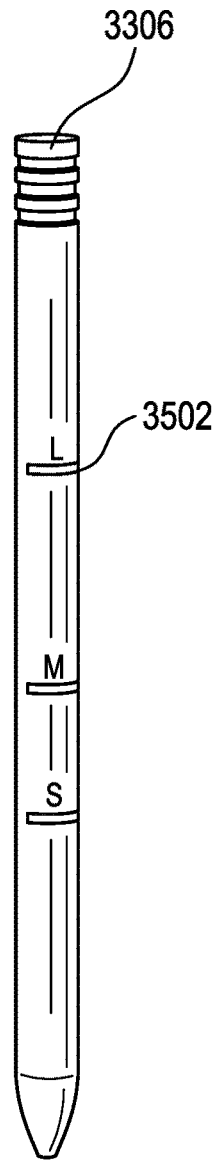
FIG. 35A is a first perspective view of a reference stick.
Figure 35B:
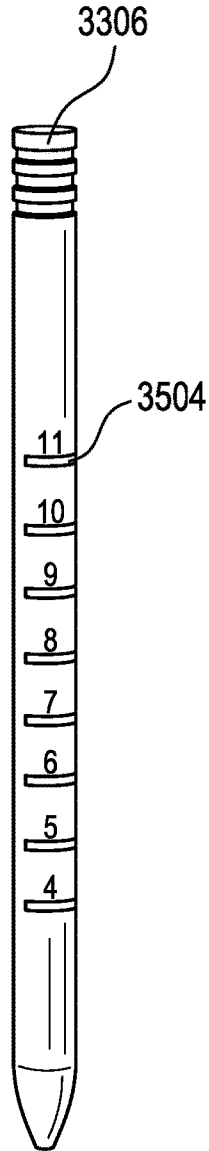
FIG. 35B is a second perspective view of a reference stick.

FIG. 34 illustrates the various sizes of surgical support instruments 3202 in greater detail. While any variety of sizes are possible, the illustrated embodiments include a larger instrument 3202a, a mid-size instrument 3202b, and a smaller instrument 3202c. In some embodiments, a difference between the difference sizes can be embodied solely in their length extending above the screw to which they couple, such that different size instruments can be chosen based on a depth of a surgical site below a patient's skin surface and a desired amount of extension of the instrument above the skin surface. The reference stick 3306 shown in FIGS. 35A and 35B can be utilized to determine the proper size of surgical support instrument 3202 to utilize for any particular patient. For example, the reference stick 3306 can be inserted into an incision formed in a patient's skin and soft tissue and advanced until it docks against a desired anatomical feature, e.g., a patient's pedicle. Looking at the "S, M, L" markings 3502 on one side of the reference stick (as shown in FIG. 35A) and noting the first marking showing above the patient's skin shows the appropriate size support instrument to use for that tissue depth. The "S, M, L" markings can be mirrored on the smaller, mid-size, and larger instruments 3202c, 3202b, 3202a, respectively. The reference stick 3306 can also include depth markings 3504 on an opposite side thereof from the surgical instrument size markings (as shown in FIG. 35B) that can advise a user of the correct length of retractor blades or tissue manipulating implements 3206 to utilize in connection with the surgical retractor 3204 coupled to the support instrument 3202.

FIGS. 36A-36D illustrate one embodiment of a surgical instrument component removal tool 3308 that can be utilized to remove a component of, e.g., a two-part surgical support instrument, such as the instrument 100 described above. As noted above, the tool 3308 can be utilized to remove, e.g., a lock body or cap 3602 of a surgical support instrument 3202, which may be desirable to provide access to a proximal portion of a bone anchor to attach a modular receiver head (not shown) thereto. As described above in connection with the lock body 104 of the instrument 100, removal of the lock body can allow a modular receiver head to be coupled to the proximal head 404 of the anchor 108. The elongate body 102 can be left in place, as it is offset from the anchor 108 by the laterally-extending projections 302a, 302b of the fork 110 and because the projections 302a, 302b disposed below the proximal head 404 will not interfere with coupling a receiver head to the proximal head of the anchor 108. Returning to FIGS. 36A-36D, utilizing the removal tool 3308 can include sliding the tool down onto a cap 3602 of a surgical support instrument 3202 in the direction of arrow 3603 until a spring button 3604 engages with the cap, as shown in FIGS. 36A and 36B. The removal tool 3308 can then be utilized to detach the cap 3602 from the shank extension 3606 by withdrawing the tool and coupled cap in the direction of arrow 3605 in FIG. 36C. To detach the cap 3602 from the tool 3308 after detachment from the shank extension 3606, a user can press the button 3604 in the direction of arrow 3607 in FIG. 36D.

In combination with the above-described distraction, any of a variety of surgical procedures can be performed utilizing the working channel provided by, e.g., the support instrument 2706 and retractor assembly 2710. For example, a user can perform a spinal fusion cage insertion procedure via the working channel between the opposed tissue manipulating implements of the retractor assembly 2710. Other exemplary procedures can include disc replacement, discectomy, endplate preparation, bone graft delivery, and the like.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The instruments disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the instruments disclosed herein can have varying degrees of rigidity or flexibility, as appropriate for their use. Device sizes can also vary greatly, depending on the intended use and surgical site anatomy. Furthermore, particular components can be formed from a different material than other components. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of spinal surgery on a human patient, it will be appreciated that the methods and devices disclosed herein can be used in any of a variety of surgical procedures with any human or animal subject, or in non-surgical procedures.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

One skilled in the art will appreciate further features and advantages based on the above-described embodiments. Accordingly, the disclosure is not to be limited by what has been particularly shown and described. All publications and references cited herein are expressly incorporated herein by reference in their entirety.

What is claimed is:

1. A surgical method, comprising:
positioning opposed projections of an elongate body of a shank extension instrument to at least partially surround a shank of an implantable anchor at a position distal of a proximal head of the anchor such that a longitudinal axis of the elongate body is laterally offset from a longitudinal axis of the anchor;
coupling the instrument to the implantable anchor by rotating a locking screw disposed within a lumen of the elongate body, the rotation of the locking screw longitudinally translating a lock body disposed adjacent to a lateral side of the elongate body, the translating of the lock body moving the lock body from an uncoupled position where the anchor is not coupled to the instrument to a coupled position where the anchor is coupled to the instrument;
coupling a retractor assembly including a plurality of tissue manipulating implements to a proximal portion of the shank extension instrument; and
retracting soft tissue by moving the plurality of tissue manipulating implements of the retractor assembly.

2. The method of claim 1, further comprising:
adjusting a position of the retractor assembly relative to the elongate body to position the plurality of tissue manipulating implements relative to tissue; and
locking a position of the retractor assembly relative to the elongate body.

3. The method of claim 1, wherein retracting soft tissue by moving the plurality of tissue manipulating implements of the retractor assembly includes translating opposed implements in a medial-lateral direction.

4. The method of claim 3, wherein retracting soft tissue by moving the plurality of tissue manipulating implements of the retractor assembly further includes toeing the opposed implements to bring distal ends thereof any of closer or father away from one another.

5. The method of claim 1, further comprising coupling a light to the retractor assembly to illuminate a workspace between the plurality of tissue manipulating implements.

6. The method of claim 1, further comprising coupling the retractor assembly to an external rigid structure.

7. The method of claim 1, wherein the retractor assembly is anchored solely to the anchor.

8. The method of claim 1, further comprising implanting the anchor in bone prior to positioning the opposed projections of the shank extension instrument to at least partially surround the shank of the anchor.

9. The method of claim 1, further comprising implanting the anchor in bone after positioning the opposed projections of the shank extension instrument to at least partially surround the shank of the anchor.

10. The method of claim 1, further comprising coupling a polyaxial receiver head to the proximal head of the anchor.

11. The method of claim 1, further comprising exerting a drag force on the head of the anchor to control polyaxial movement of the shank extension instrument relative to the anchor.

12. The method of claim 11, wherein exerting a drag force on the head of the anchor includes translating the lock body relative to the elongate body to contact an upper portion of the proximal head of the anchor.

13. The method of claim 1, wherein the locking screw translates in a longitudinal direction with respect to the elongate body and wherein the lock body translates in a same direction as the locking screw.

14. The method of claim 1, wherein a biasing element disposed within a lumen of the elongate body and urges the lock body in a distal direction.

15. The method of claim 14, wherein the biasing element urges the lock body into contact with the anchor head to exert a drag force on the anchor.

16. The method of claim 1, comprising inserting a locking pin of the retractor assembly into one of a plurality of holes formed in the proximal portion of the elongate body to selectively lock the retractor assembly at a corresponding one of a plurality of positions along the length of the proximal portion of the elongate body.

17. The method of claim 1, wherein the proximal portion of the elongate body includes a ratchet configured to interface with a pawl coupled to the retractor assembly to selectively lock the retractor assembly at a plurality of positions along the proximal portion of the elongate body.

18. The method of claim 1, comprising laterally translating at least one of the plurality of tissue manipulating implements relative to the longitudinal axis of the elongate body.

19. The method of claim 18, comprising pivoting at least one of the plurality of tissue manipulating implements about an axis that is transverse to the longitudinal axis of the elongate body.

20. The method of claim 1, wherein at least a portion of the lock body extends longitudinally along the lateral side of the elongate body and distally beyond a portion of the elongate body in with the locking screw is disposed.

* * * * *